(12) United States Patent
Rinehart et al.

(10) Patent No.: US 11,413,395 B2
(45) Date of Patent: Aug. 16, 2022

(54) SYSTEMS AND METHODS FOR MONITORING AND CONTROLLING FLUID INFUSION TO A PATIENT

(71) Applicant: Perceptive Medical Inc., Newport Beach, CA (US)

(72) Inventors: Joseph Rinehart, Newport Beach, CA (US); Douglas Patton, Newport Beach, CA (US); Morgan McKeown, Kailua, HI (US)

(73) Assignee: Perceptive Medical Inc., Newport Beach, CA (US)

( * ) Notice: Subject to any disclaimer, the term of this patent is extended or adjusted under 35 U.S.C. 154(b) by 0 days.

(21) Appl. No.: 17/550,458

(22) Filed: Dec. 14, 2021

(65) Prior Publication Data

US 2022/0184304 A1   Jun. 16, 2022

Related U.S. Application Data

(60) Provisional application No. 63/125,273, filed on Dec. 14, 2020.

(51) Int. Cl.
*A61M 5/172*   (2006.01)
*G16H 10/60*   (2018.01)
(Continued)

(52) U.S. Cl.
CPC ............ *A61M 5/1723* (2013.01); *A61B 5/743* (2013.01); *G05B 7/02* (2013.01); *G16H 10/60* (2018.01); *G16H 15/00* (2018.01); *G16H 20/10* (2018.01); *G16H 40/63* (2018.01); *G16H 50/70* (2018.01); *A61M 2205/18* (2013.01); *A61M 2205/505* (2013.01); *A61M 2230/04* (2013.01); *A61M 2230/30* (2013.01)

(58) Field of Classification Search
None
See application file for complete search history.

(56) References Cited

U.S. PATENT DOCUMENTS

2020/0005916 A1\*   1/2020   Brooks ................ G16H 50/50
2020/0093988 A1    3/2020   Zhong et al.
(Continued)

OTHER PUBLICATIONS

European Patent Office, International Search Report and Written Opinion, dated Apr. 14, 2022.

*Primary Examiner* — Manuel A Mendez
(74) *Attorney, Agent, or Firm* — Ryan Dean; Umberg Zipser LLP

(57) ABSTRACT

Systems and methods are described for presenting information for managing a vital sign of a patient. A graphical user interface (GUI) can be presented that displays information concerning a vital sign of a patient, including the most current value of the vital sign received and past values of the vital sign over an elapsed time period. Using this information, a time in target value can be generated representing an amount of elapsed time the patient's measured vital sign was within a predetermined range. Preferably, the systems and methods are used with a closed-loop system that may automatically adjust a dosage rate of a medication, although manual control is also contemplated. The GUI may comprise one or more visual indicators presented on the historical data that, when selected, present additional information that may be useful to managing the care of the patient.

30 Claims, 27 Drawing Sheets

(51) Int. Cl.
*G16H 15/00* (2018.01)
*G16H 50/70* (2018.01)
*G16H 20/10* (2018.01)
*G16H 40/63* (2018.01)
*A61B 5/00* (2006.01)
*G05B 7/02* (2006.01)

(56) References Cited

U.S. PATENT DOCUMENTS

2020/0227158 A1 7/2020 Schwalb et al.
2020/0305713 A1 10/2020 Sipe et al.

* cited by examiner

SYSTEMS AND METHODS FOR MONITORING AND CONTROLLING FLUID INFUSION TO A PATIENT

This application claims priority to U.S. provisional patent application having Ser. No. 63/125,273 filed on Dec. 14, 2020. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is graphic user interfaces, and in particular, those user interfaces for use with fluid infusion devices.

BACKGROUND

The following description includes information that may be useful in understanding the present invention. It is not an admission that any of the information provided herein is prior art or relevant to the presently claimed invention, or that any publication specifically or implicitly referenced is prior art.

Various pumps exist for fluid infusion to a patient. One of the most common are gravity infusion devices, which utilize gravity to deliver medication. However, such devices are unable to provide precise dosage rates and any information concerning the fluid to be infused.

In an attempt to address these deficiencies, various companies offer volumetric pumps that allow for more precise dosage rates. For example, ALARIS® offers its CAREFUSION® infusion pumps that can provide different dosage rates for multiple medications. Among other problems, such pumps are typically bulky, can be difficult to use, and have a limited user interface.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved user interfaces for infusion devices that are easier to use and access pertinent patient information.

SUMMARY OF THE INVENTION

The inventive subject matter provides apparatus, systems, and methods for graphic user interfaces (GUIs) for intravenous (IV) infusion devices. Contemplated IV infusion devices can comprise a pump unit communicatively coupled with a display screen, which can be configured to present information concerning a patient and a medication delivery, for example.

Preferably, the display screen is a touch-screen display screen or otherwise configured to allow input of commands from a medical professional. For example, using the display screen, it is contemplated that a dosage of medication being administered to a patient can be varied or various settings concerning infusion of a medication to a patient can be reviewed or changed. Such settings may include, for example, a minimum dose amount, a maximum dose amount, a concentration of a medication, a type of medication, the patient's age, the patient gender, the patient's weight, a target range for a vital sign of the patient, a focus for the vital sign, and so forth.

The display screen could be configured to present various information concerning the patient including, for example, a minimum dose amount of the medication, a maximum dose amount of the medication, a current dosage rate of the medication, historical dosage rates of the medication, a concentration of the medication, a type of the medication, a preferred range of the vital sign including maximum and minimum values, the focus for the vital sign, a current value of the vital sign, historical values of the vital sign, a time in target, a remaining amount of the medication, and so forth.

As described above, the GUI could be part of a system or method for managing a vital sign of a patient. Such system, for example, could include the GUI. In addition, the system may comprise a receiver adapted to receive information from a first source concerning a vital sign of a patient, and a processor communicatively linked to the receiver to obtain the information from the first source and to the GUI to control a display of the information on the GUI. The processor is preferably configured to present information concerning the vital sign and a medication being administered to the patient on the GUI.

Various objects, features, aspects, and advantages of the inventive subject matter will become more apparent from the following detailed description of preferred embodiments, along with the accompanying drawing figures in which like numerals represent like components.

DETAILED DESCRIPTION

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

FIGS. 1A-24 illustrate various embodiments of a graphical user interface (GUI) for managing a vital sign and medication for patient.

Figure 1A:
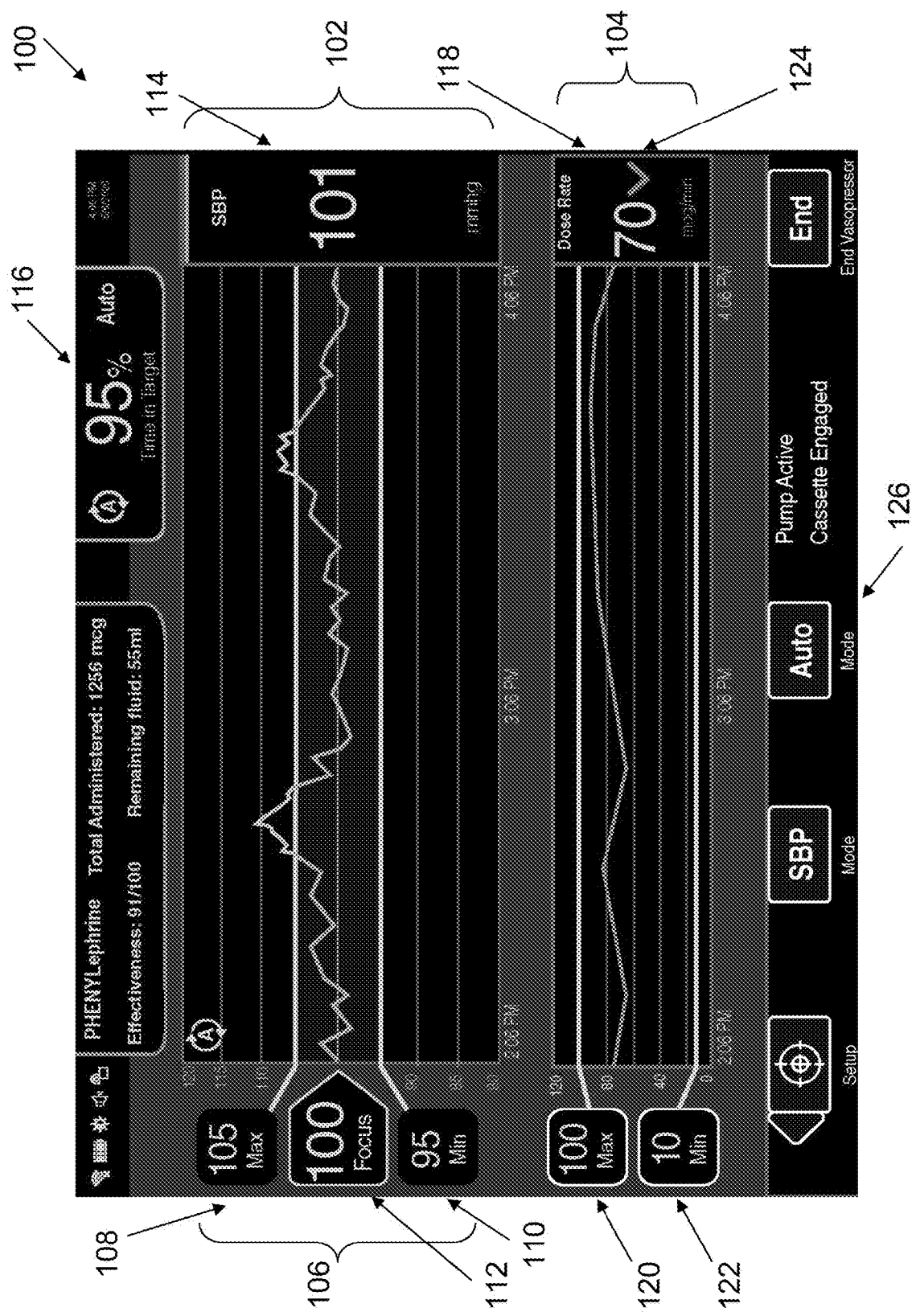
FIG. 1A illustrates one embodiment of an exemplary GUI presented on a display screen.

As shown in FIG. 1A, an exemplary GUI 100 can be presented on a display screen of a device, for example. The GUI 100 can display a patient's vital sign information 102 and dosage rate information 104 of a medication being administered to the patient. The vital sign information 102 may include, for example, a current vital sign of the patient received from a first source as well as historical data relating to the patient's vital sign based on prior information received from the first source. As shown in FIG. 1A, the GUI 100 displays the current blood pressure (101) of the patient as well as a graph of the blood pressure values over the past two hours. Of course, it is contemplated that the specific amount of time of past values could be altered as desired.

The GUI 100 can further display or present a predetermined or preferred range 106 of the vital sign of the patient, which may be defined by a minimum value 110 and a maximum value 108. In some embodiments, it is contemplated that the vital sign values of the patient that fall within the predetermined range 106 can be shown in a first color and the vital sign values of the patient that fall outside of the predetermined range 106 can be shown in a different color. In this manner, a clinician can quickly see at which times and for how long the patient's vital sign has fallen outside of the range 106.

The GUI 100 may also include a focus value 112 for the vital sign which, like the predetermined range 106, can be set and/or changed by the clinician or other medical professional. It is contemplated that the focus value 112 can be used with an algorithm to determine a dosage rate of the medication based on the patient's information. An exemplary algorithm is described in co-pending U.S. patent application having Ser. No. 17/365,730 filed on Jul. 1, 2021, which is hereby incorporated by reference herein in its entirety.

As new vital signs are received from the first source, it is contemplated that the latest vital sign can be presented as the current vital sign 114 and the prior vital sign can be saved to the historical data and presented on the GUI 100.

Figure 4:
FIG. 4 illustrates one embodiment of an exemplary GUI for adjusting a time period for a chart of historical data.

As shown, the historical data of the vital sign is preferably plotted or graphed on the GUI 100 for quick review of the patient's vital sign information 102. In this manner, the historical data can depict the patient's vital sign information 102 over an elapsed time period. It is contemplated that the specific time period of historical data shown can be changed by the clinician or other medical professional by selecting a time period object on the GUI 100. Selecting the object can open a pop-up window or other present a revised interface to select the new time period. An exemplary embodiment of such an interface 400 is shown in FIG. 4.

A time in target percentage 116 or another indicator can also be displayed on the GUI 100. This time in target value 116 shown in FIG. 1A represents the percentage of time the patient's vital sign has remained within the predetermined range 106 during the time period shown on the GUI 100. To calculate the time in target value 116, a first set of vital signs can be generated by selecting items of the historical data falling within a predefined time period, which may match the elapsed time period of historical vital sign information shown on the GUI 100. An amount of time that the first set of vital signs were within the predetermined range 106 can be determined or estimated, and the amount of time is divided by the predefined time period. As shown in FIG. 1A, the time in target value 116 (e.g., 95%) is presented for the automated management of the patient's vital sign. The target value 116 advantageously allows the clinician to quickly understand the percentage of time the patient's vital sign was maintained within the predetermined range 106.

Figure 2:
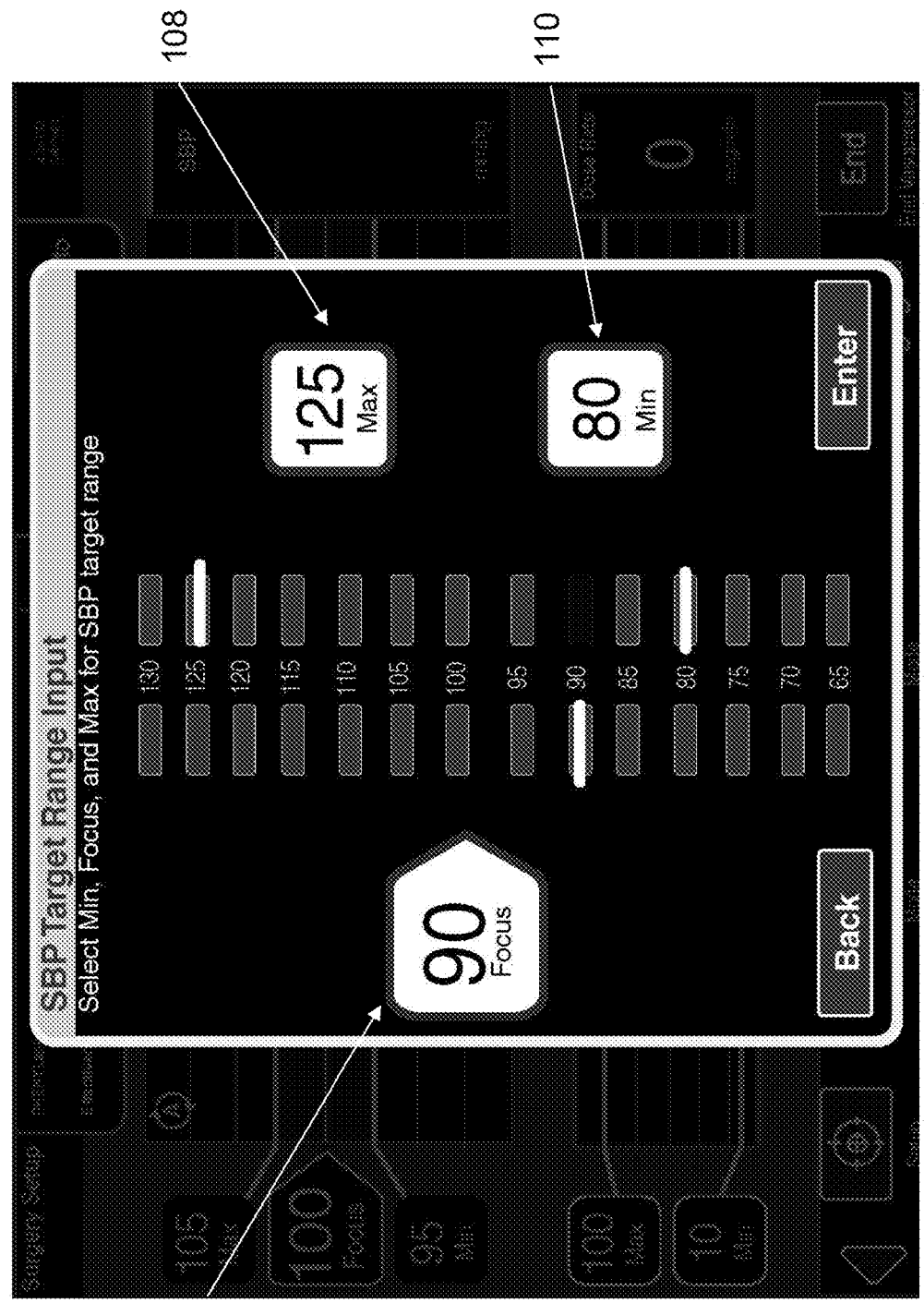
FIG. 2 illustrates one embodiment of an exemplary GUI for adjusting a predefined range of values and a focus value of a vital sign of a patient.

The GUI 100 can comprise various other objects to allow for setting of the minimum value 110 and the maximum value 108, as well as the focus value 112. For example, it is contemplated that the minimum value 110, the maximum value 108, and the focus value 112 can each be, or collectively can be, a selectable object, and once selected a pop-up window or other change to the GUI 100 can be presented that allows one or more of the values to be adjusted. Alternatively, it is contemplated that a specific area about those values can be selectable. FIG. 2 illustrates one embodiment of an interface 200 that can be presented when an object is selected to vary the minimum value 110, the maximum value 108, and/or the focus value 112.

Figure 3:
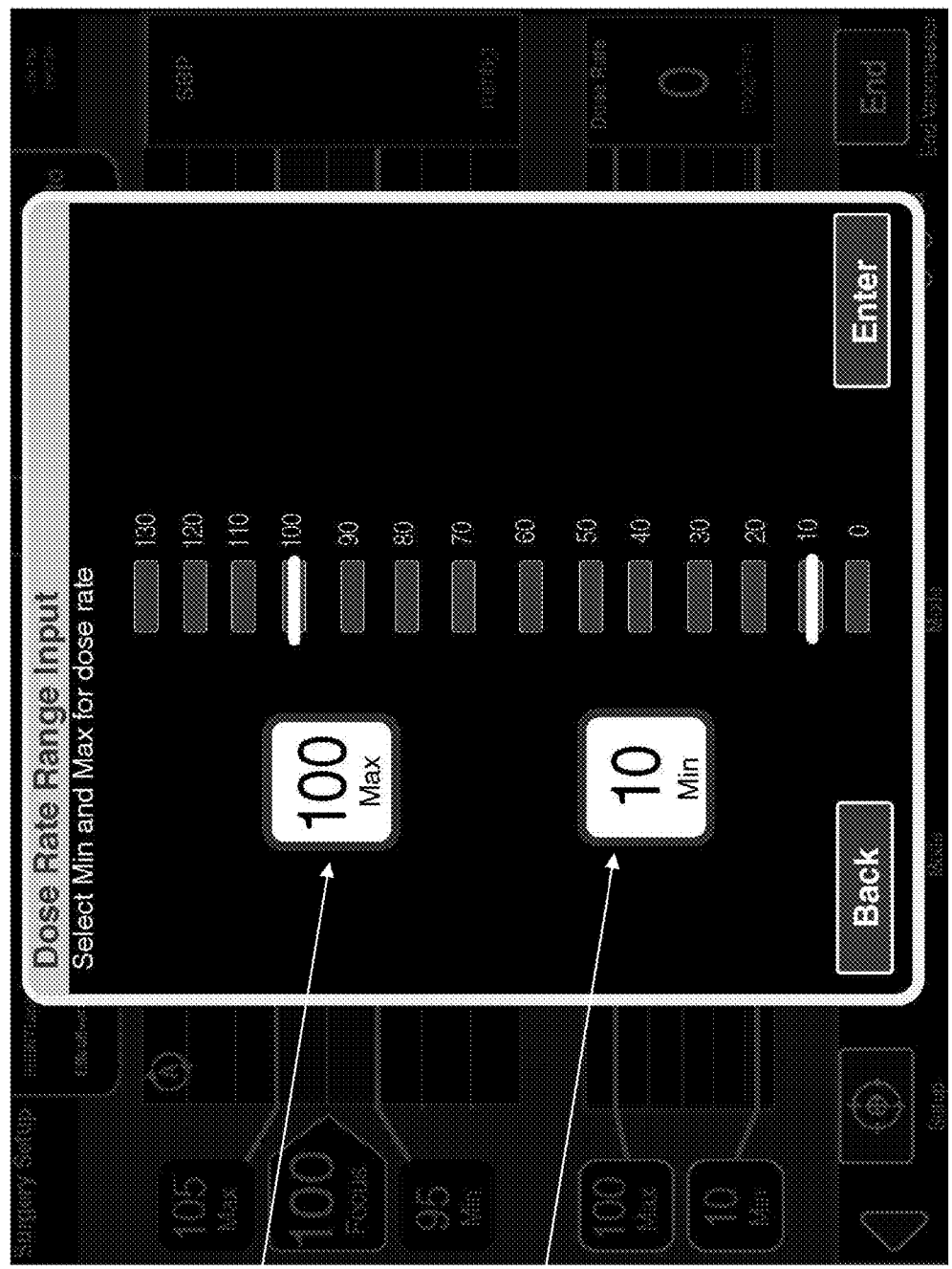
FIG. 3 illustrates one embodiment of an exemplary GUI for adjusting a minimum and maximum values of a dosage rate of a medication.

As shown in FIG. 1A, the GUI 100 can further display information 104 concerning a dosage of medication being administered to the patient. For example, a current dosage rate 118 of the medication being administered can be displayed as well as a minimum dosage rate 122 and a maximum dosage rate 120 of the medication. The minimum dosage rate 122 and the maximum dosage rate 120 can be selected by selecting a dosage rate object on the GUI 100, which can generate a pop-up or other interface for changing one or both of the minimum dosage rate 122 and the maximum dosage rate 120. For example, it is contemplated that the minimum dosage rate 122 and the maximum dosage rate 120 can each be, or collectively can be, a selectable object, and once selected a pop-up window or other change to the GUI 100 can be presented that allows one or more of the values to be adjusted. Alternatively, it is contemplated that a specific area about the values can be selectable. FIG. 3 illustrates one embodiment of an interface 300 that can be presented when an object is selected to vary the minimum dosage rate 122 and/or the maximum dosage rate 120.

As shown in FIG. 1A, it is contemplated that the current dosage rate 118 and historical dosage rates of the medication can be plotted, graphed, or otherwise presented on the GUI 100 for an elapsed time period. This advantageously allows the clinician or other medical professional to quickly be apprised of changes to the dosage rate over time, and whether the dosage rate has significantly increased or decreased despite the patient's vital sign remaining within the predetermined range 104. It is contemplated that the specific time period of historical data shown can be changed by the clinician or other medical professional by selecting a time period object on the GUI 100. Selecting the object can open a pop-up window or other present a revised interface to select the new time period. An exemplary embodiment of such an interface 400 is shown in FIG. 4.

In some embodiment, a dosage change indicator 124 can be generated and presented on the GUI 100, which is shown next to the current dosage rate 118 in FIG. 1A. The dosage change indicator 124 represents a trend line between the current dosage rate of the medication and historical data and may show that the dosage rate has changed slightly, drastically, or not at all, as well as the general direction (e.g., increase or decrease of the dosage rate). As shown in FIG. 1A, the dosage change indicator 124 may be represented visually by one or more arrows, but could be represented by other shapes or objects, colors, or otherwise.

Such an indicator could also be displayed for the vital sign information 102, such as to show how the vital sign is changing over time.

In some embodiments, it is contemplated that the GUI 100 may also present a remaining amount of medication, which can be estimated as a function of an initial volume of medication, the current dosage rate, and any historical dosage rate data, and the estimated remaining amount of medication can be presented on the GUI 100.

Figure 9:
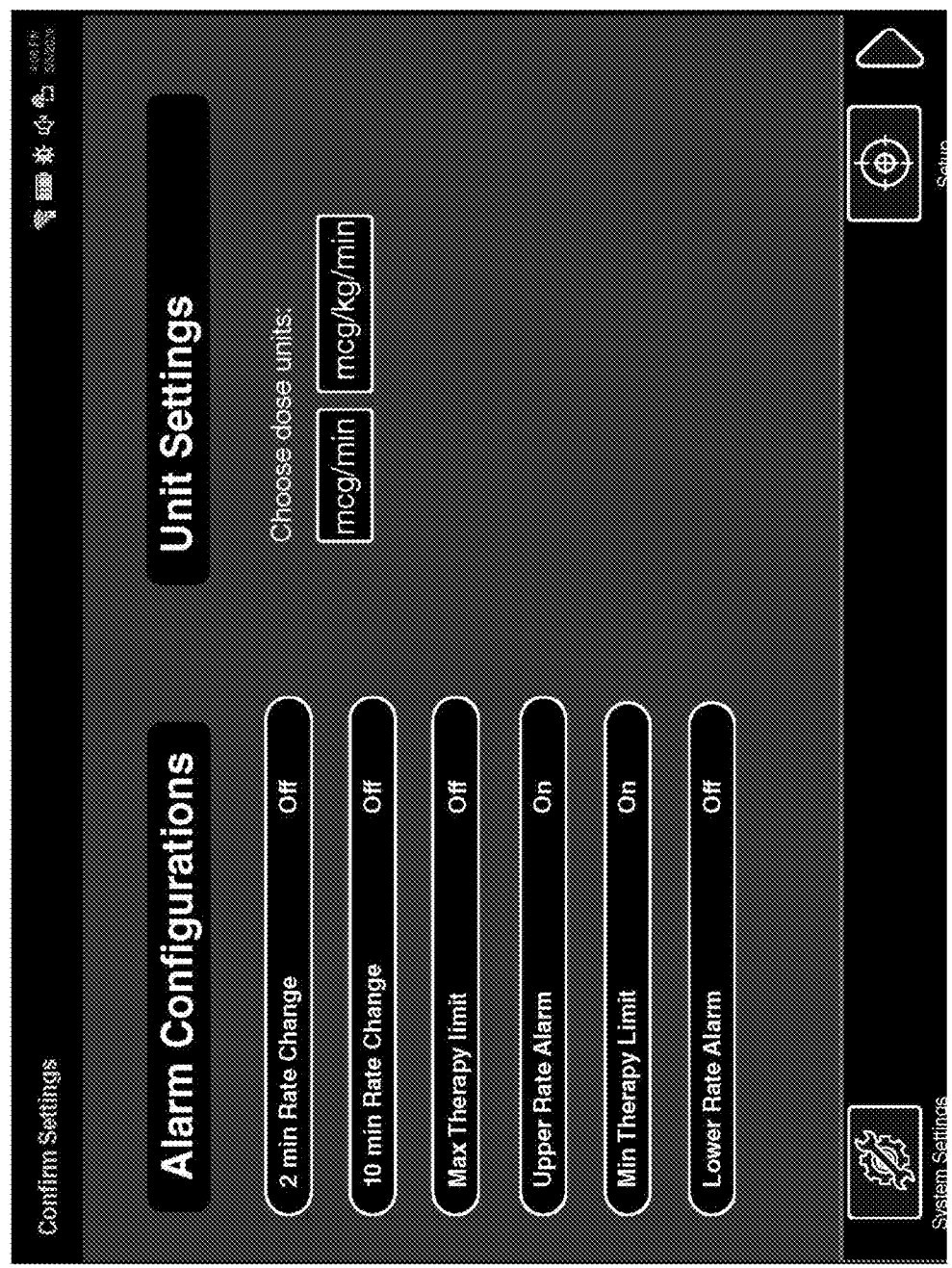
FIG. 9 illustrates one embodiment of an exemplary interface for configuring alarm settings.

It is contemplated that various alarm conditions could be selected or modified using an alarm interface 900 such as shown in FIG. 9. When an alarm is received or generated, it is contemplated that an alert could be presented on the GUI 100, for example. Such alert could comprise a visual indicator on the GUI 100, such as varying the color of one or more objects and/or some or all of the background, a pop-up window, or other indicators.

Figure 10:
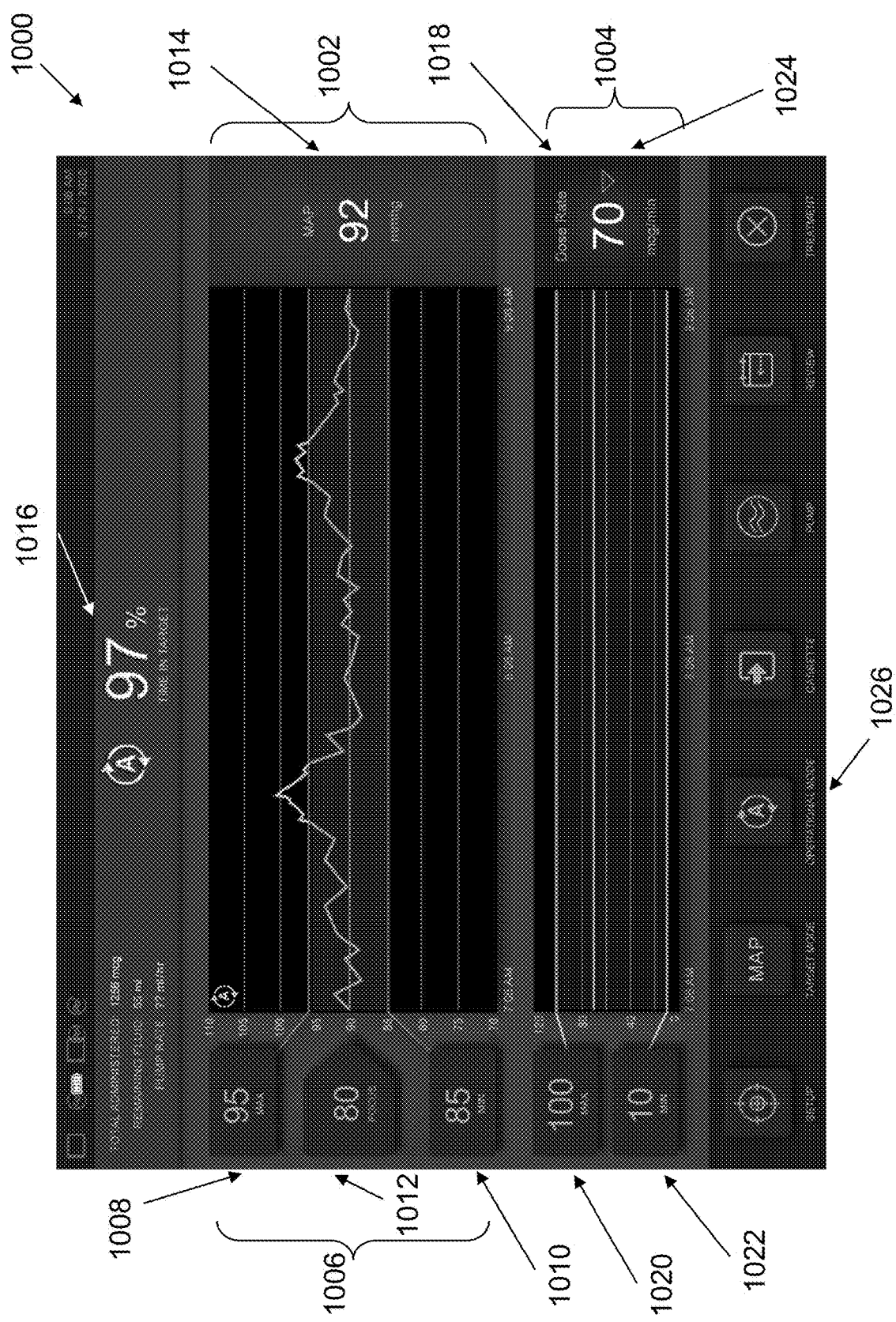
FIG. 10 illustrates another embodiment of an exemplary GUI presented on a display screen.

For example, FIG. 10 illustrates one embodiment of a GUI 1000 having various visual indicators that could be used to illustrate whether the vital sign is within, or how much it is outside of, the predetermined range. For example, it is contemplated that the area behind the vital sign value 1014 could be shaded or presented in a specific color to indicate a status of the vital sign (e.g., green is within range, yellow is within a predetermined amount or percentage outside of the range, and red is outside of the determined amount or percentage outside of the range). It is also contemplated that the graph lines themselves and/or the background behind the graph could be shaded or colored to indicate whether the vital sign is within the predetermined range.

It is contemplated that alerts could be generated for various reasons including, for example, if the current dosage rate 1018 falls outside of the predetermined range defined by the minimum dosage rate 1022 and the maximum dosage rate 1020 of the medication, if the current vital sign 1014 falls outside of the predetermined range 1006, if the time in target value 1016 is less than a predetermined threshold, and/or based on a signal received from a second source.

In some embodiments, it is further contemplated that the GUI 100 could change depending on how long and to what degree of check-in is required by a user. Thus, for example, a yellow color could indicate that a user should check in eventually based on a patient's vital sign or a length of time elapsed since last check in, for example. Similarly, a red color could indicate that a user should check in now. It is further contemplated that the color or other aspects of the GUI 100 could vary over time to indicate when check-in may be required in the future.

Exemplary hardware that could be used in conjunction with the GUIs discussed herein is described in co-pending U.S. non-provisional application having Ser. No. 17/529,691 filed on Nov. 18, 2021.

Figure 5:
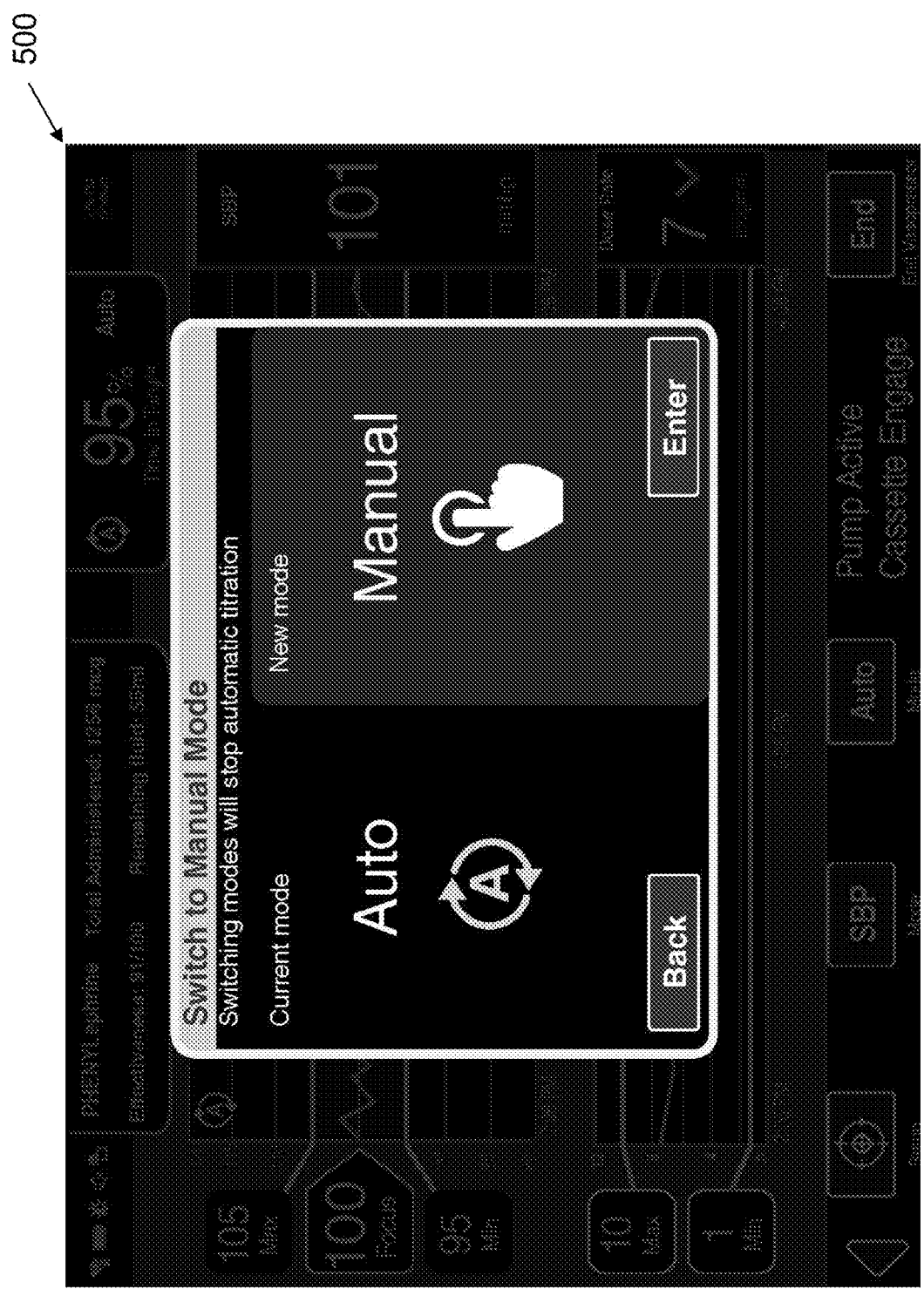
FIG. 5 illustrates one embodiment of an exemplary interface that can be presented to change a mode of operation from automated control to manual control.

As shown in FIG. 1A, the system is operating in an automated mode and the interface is configured accordingly. At the bottom center of FIG. 1A, an automated/manual management object 126 can be presented on the GUI 100, which can allow the system to switch from a closed-loop automated system for managing the vital sign and the current dosage rate to a manual system by selecting the object 126. In some embodiments, upon selecting the automated/manual management object 126, a new interface or pop-up window can be presented to allow the system's mode to be changed. FIG. 5 illustrates an exemplary interface 500 that can be presented upon selecting the object.

Figure 1B:
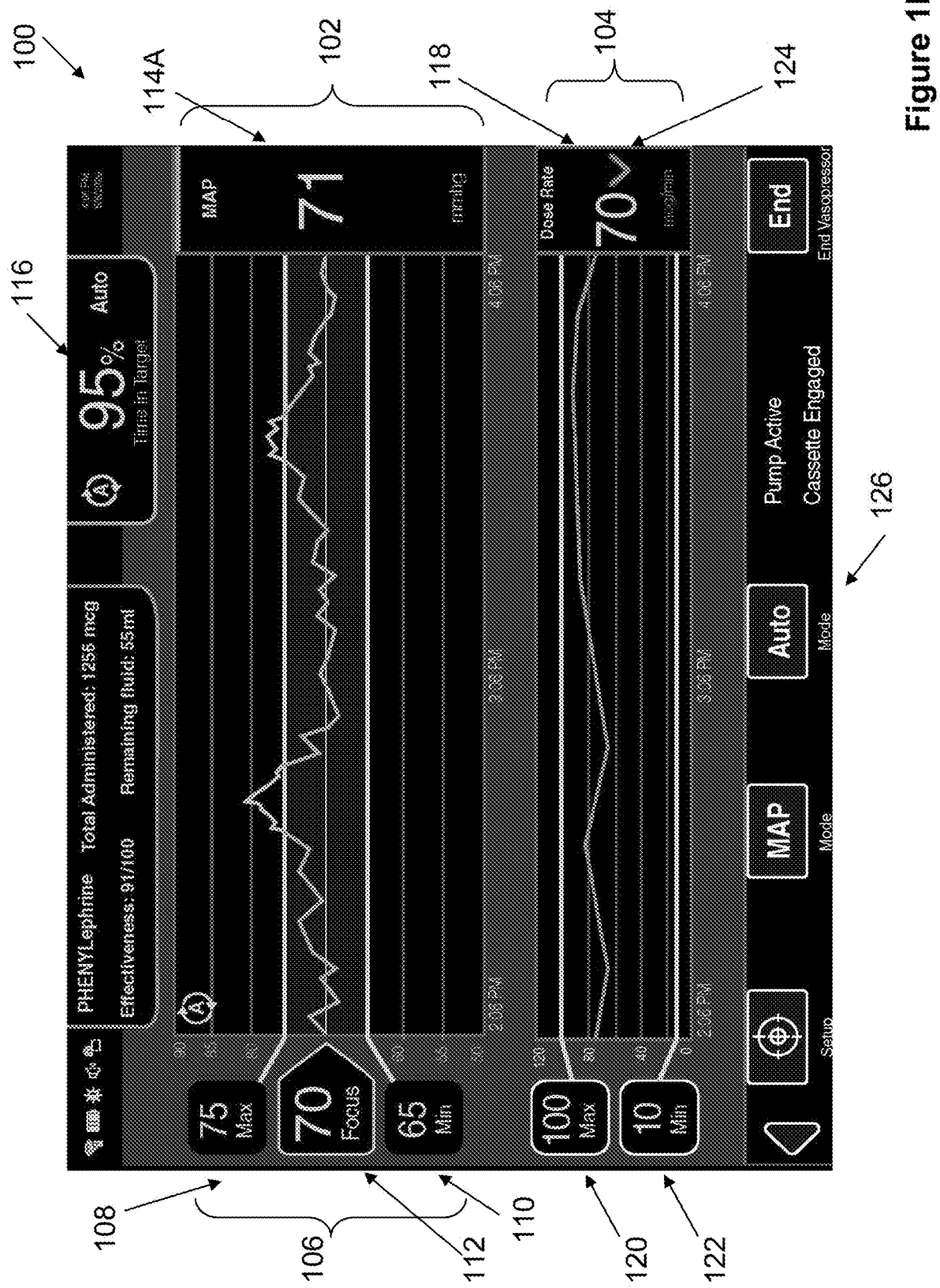
FIG. 1B illustrates another embodiment of an exemplary GUI presented on a display screen.

FIG. 1B illustrates the GUI 100 with the patient's vital sign 114A represented as mean arterial pressure (MAP) rather than systolic blood pressure (SBP) as in FIG. 1A. In such situations, it is contemplated that the first source sensing the patient's vital sign may comprise a transducer attached to the patient. However, the specific vital sign and first source detecting the vital sign could be varied without departing from the scope of the invention herein. With respect to the remaining numerals in FIG. 1B, the same considerations for like components with like numerals of FIG. 1A apply.

FIG. 2 illustrates an exemplary embodiment of a GUI 200 or pop-up window that allows a clinician or other medical professional to adjust a predefined range of values (e.g., a minimum value of range 110 and a maximum value of range 108) and a focus value 112 of a vital sign of a patient.

FIG. 3 illustrates an exemplary embodiment of a GUI 300 or pop-up window that allows a clinician or other medical professional to adjust a minimum value 122 and a maximum value 120 of a dosage rate of a medication.

FIG. 4 illustrates an exemplary embodiment of a GUI 400 or pop-up window that allows a clinician or other medical professional to adjust a length of a time period of values to present on the chart of historical data shown in FIG. 1A for example.

If the clinician or other medical professional decides to switch from the automated mode where the dosage rate of the medication is adjusted automatically to a manual mode where the dosage rate of the medication is adjusted manually, it is contemplated that a different interface can be presented or displayed to represent the change in mode and visually indicate the amount or portion of time the control is in manual mode and the amount or portion of time the control was in the automated mode. One embodiment of such an interface 600 is shown in FIG. 6.

Figure 6:
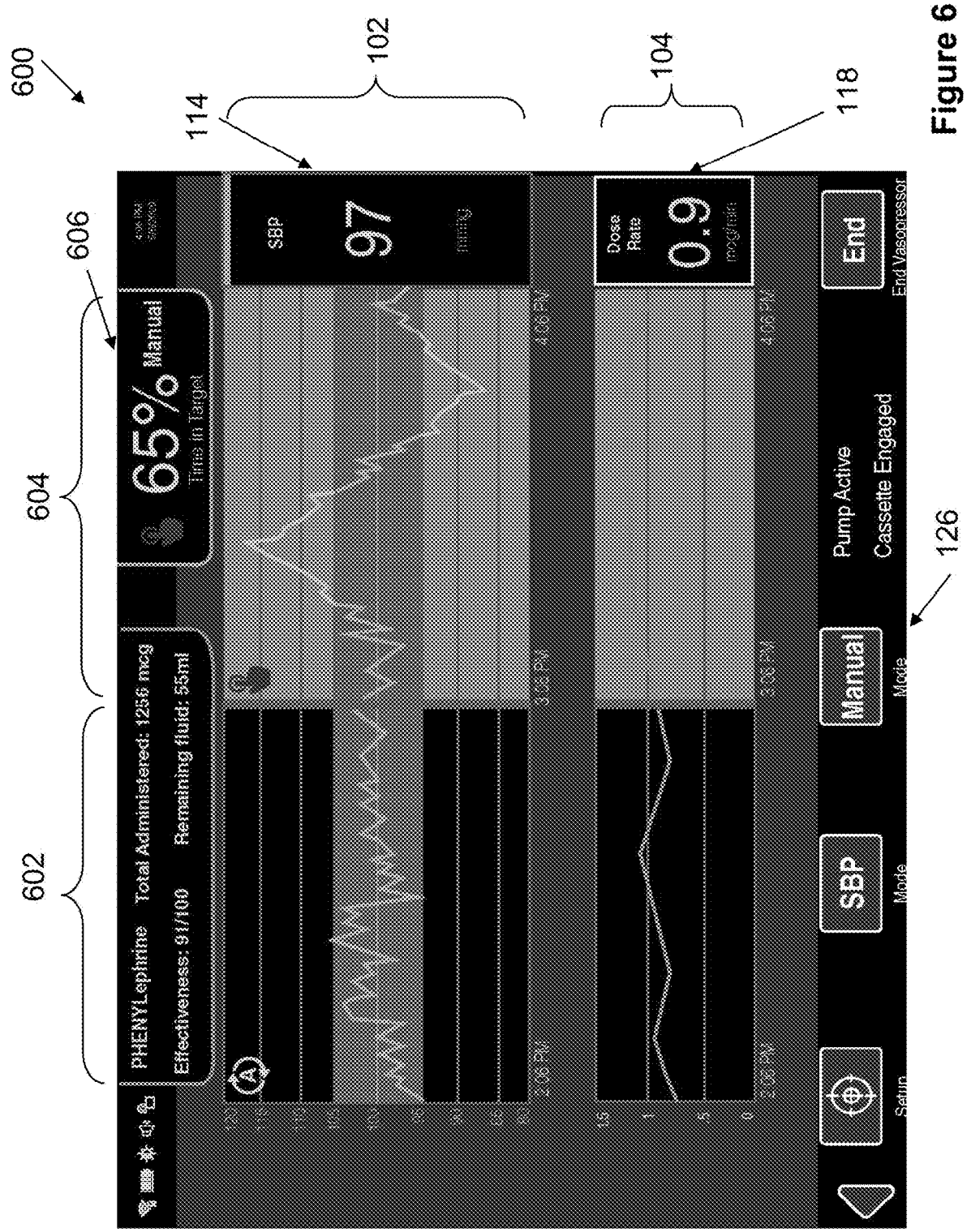
FIG. 6 illustrates one embodiment of an exemplary GUI indicating when the control was automated and when the control was manual.

As can be seen in FIG. 6, the GUI 600 presents a graph of historical data that is visually divided into a first portion of time 602 when the control was in the automated mode and a second portion of time 604 when the control was in the manual mode. Of course, there may be three or more time periods depending on the elapsed time shown and the number of times the mode was switched during that time period.

Where both automated and manual modes are utilized, it is preferred that a second time in target value 606 is presented that represents the time the patient's vital sign has been within the predetermined range while the system/control is in manual mode. To calculate the second time in target value 606, a second set of vital signs can be generated by selecting items of the historical data falling within a second predefined time period, which may match the elapsed time period of historical vital sign information for the manual mode shown on the GUI 600. An amount of time that the second set of vital signs were within a predetermined range can be determined or estimated, and the amount of time is divided by the second predefined time period.

As shown in FIG. 6, the time in target value 606 (e.g., 65%) is presented for the manual management of the patient's vital sign (e.g., during manual mode) and may include the word manual afterwards to indicate this mode. Such value 606 advantageously allows the clinician or other medical professional to quickly understand how often the patient's vital sign was maintained within the predetermined range 606 while in manual control.

It is especially preferred that the GUI 600 may display both a first time in target value 116 while in an automated mode and the second time in target value 606 while in a manual mode to allow the clinician or other medical professional to quickly compare the two values. With respect to the remaining numerals in FIG. 6, the same considerations for like components with like numerals of FIG. 1A apply.

Figure 7:
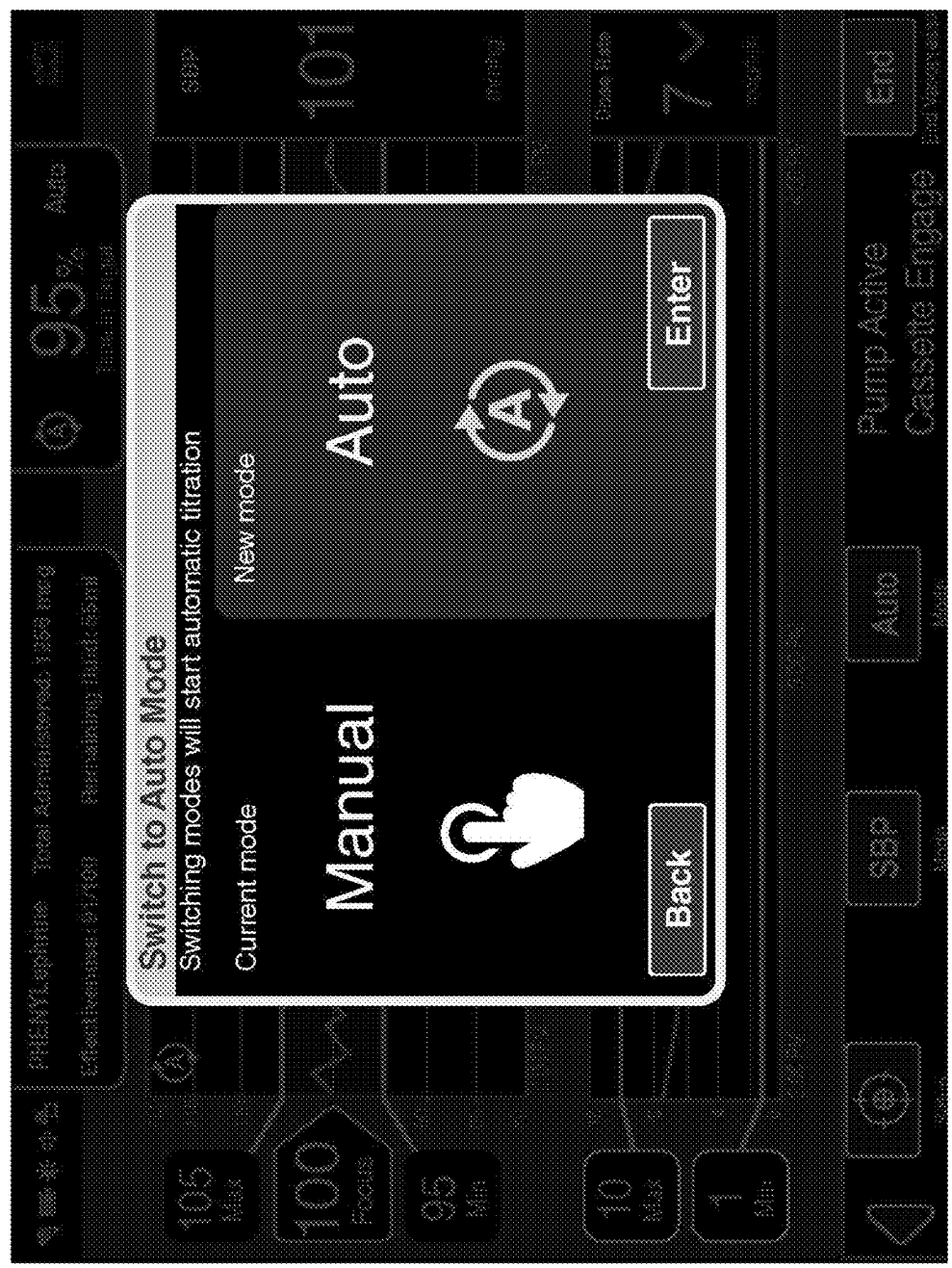
FIG. 7 illustrates one embodiment of an exemplary interface that can be presented to change a mode of operation from manual control to automated control.

It is further contemplated that a clinician or other medical professional may switch back to the automated, closed-loop system by selecting the automated/manual management object 126 presented on the GUI 600. In some embodiments, upon selecting the automated/manual management object 126, a new interface or pop-up window can be presented to allow the system's mode to be changed. FIG. 7 illustrates an exemplary interface 700 that allows a clinician or other medical professional to switch between manual and automated modes.

Figure 8:
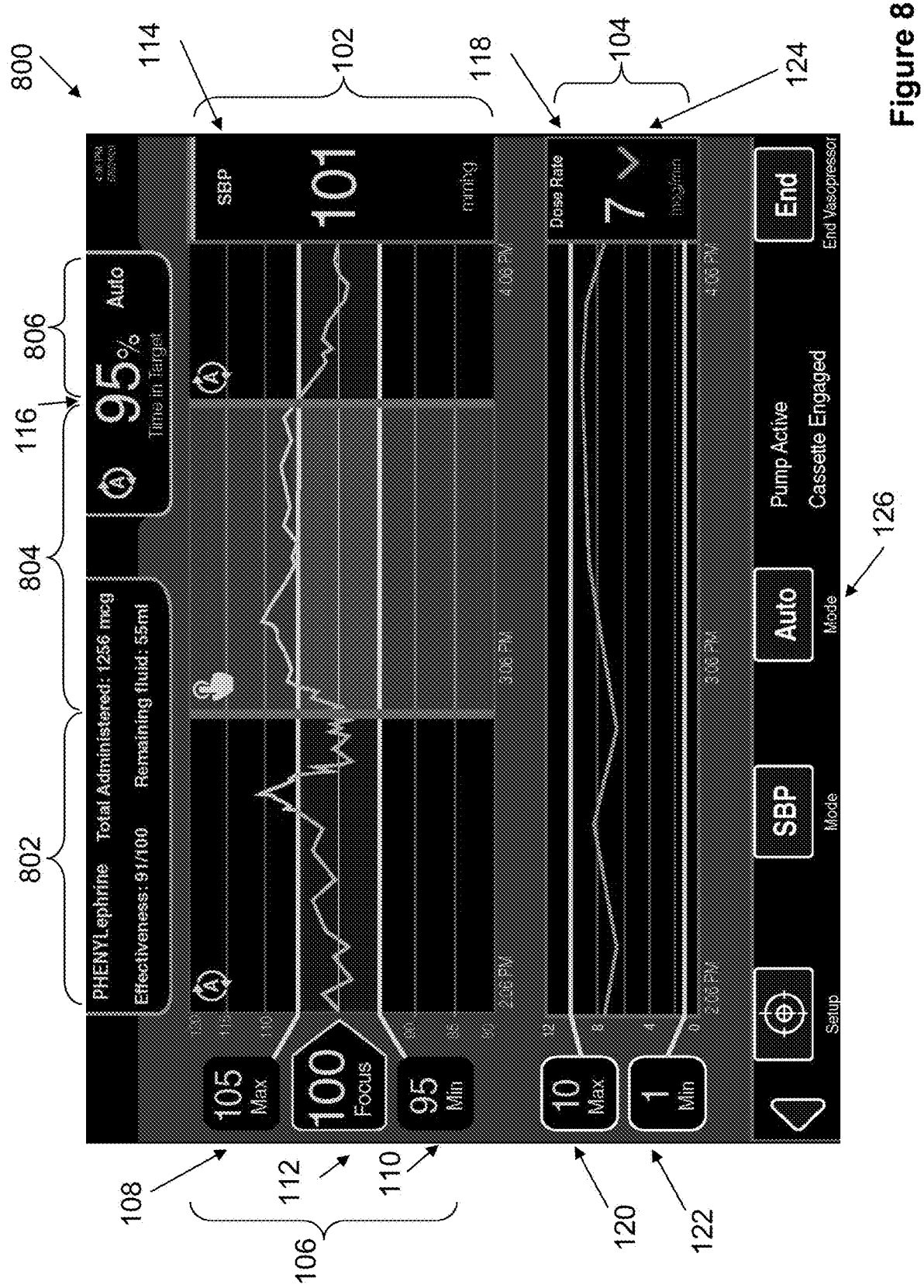
FIG. 8 illustrates another embodiment of an exemplary interface that can be presented to change a mode of operation from manual control to automated control.

FIG. 8 illustrates another embodiment of a GUI 800 that differentiates values of the vital sign and operation of the system between the automated control mode and the manual control mode. As shown in FIG. 8, the GUI 800 presents a first portion of time 802 the control was in the automated mode, a second portion of time 804 the control was in the manual mode, and a third portion of time 806 the control was in the automated mode. It is preferred that a time in target value 116 is presented that represents the time the patient's vital sign has been within the predetermined range while the system/control is in current mode (here, automated mode). The time in target value 116 (e.g., 95%) is presented for the automated management of the patient's vital sign and may include the word "Auto" or "Automated" afterwards to indicate the current mode. As seen, the mode can also be indicated by the "A" symbol shown to the left of the time in target value 116.

As discussed above with reference to FIG. 6, the GUI 800 may display both the time in target value 116 while in an automated mode and a second time in target value representing a percentage of time the patient's vital sign was in the predetermined range while in the manual control mode to allow the clinician or other medical professional to quickly compare the two values. With respect to the remaining numerals in FIG. 8, the same considerations for like components with like numerals of FIG. 1A apply.

Figure 11:
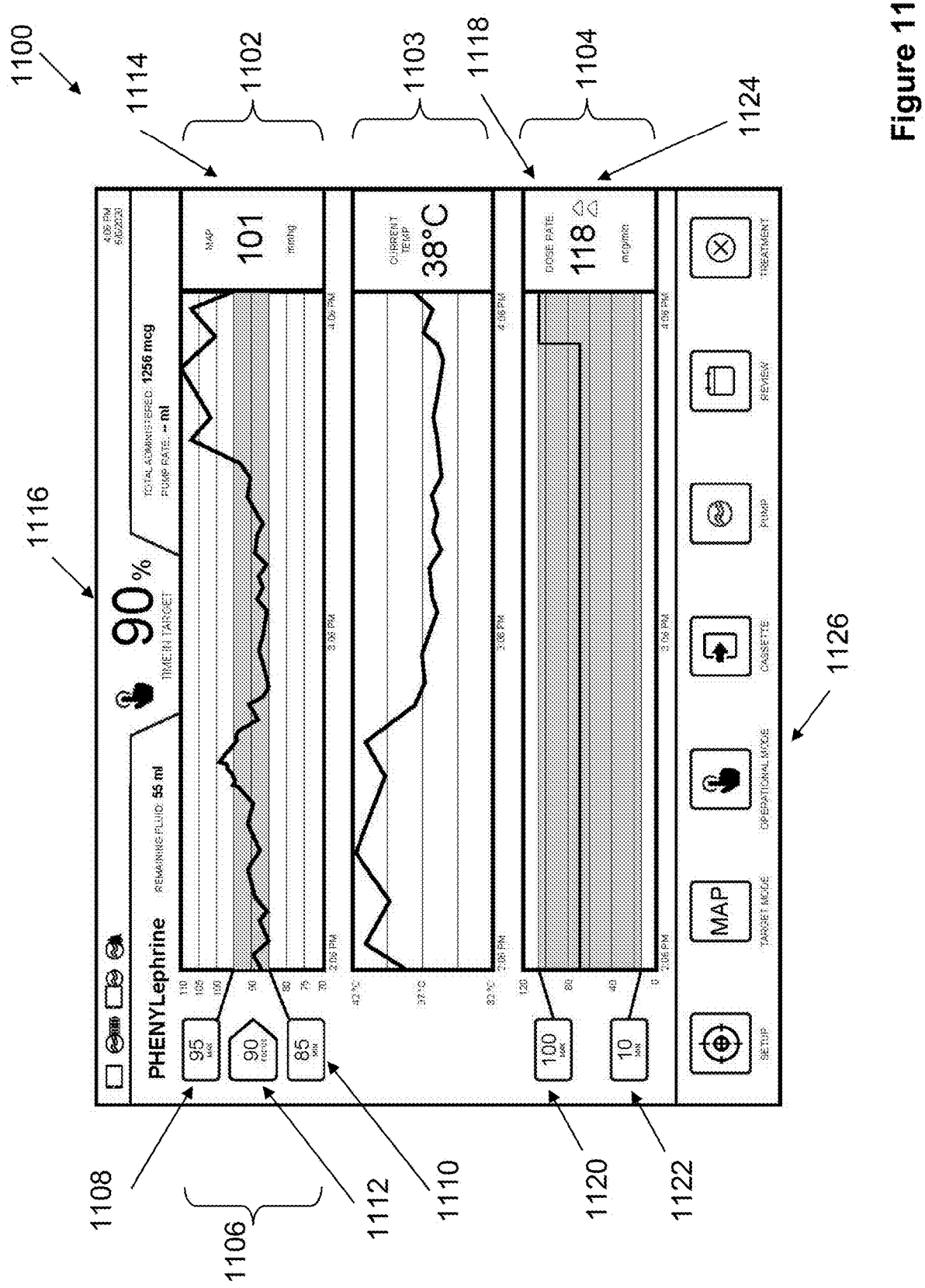
FIG. 11 illustrates another embodiment of an exemplary GUI presented on a display screen.

FIG. 11 illustrates another embodiment of a GUI 1100 that can be presented on a display screen, for example. The GUI 1100 can display vital sign information 1102 of a patient and dosage rate information 1104 of a medication being administered to the patient. The vital sign information 1102 may include, for example, a current vital sign of the patient received from a first source (such as a transducer or other sensor) as well as a chart/graph of historical data relating to the patient's vital sign based on prior information received from the first source.

Figure 12:
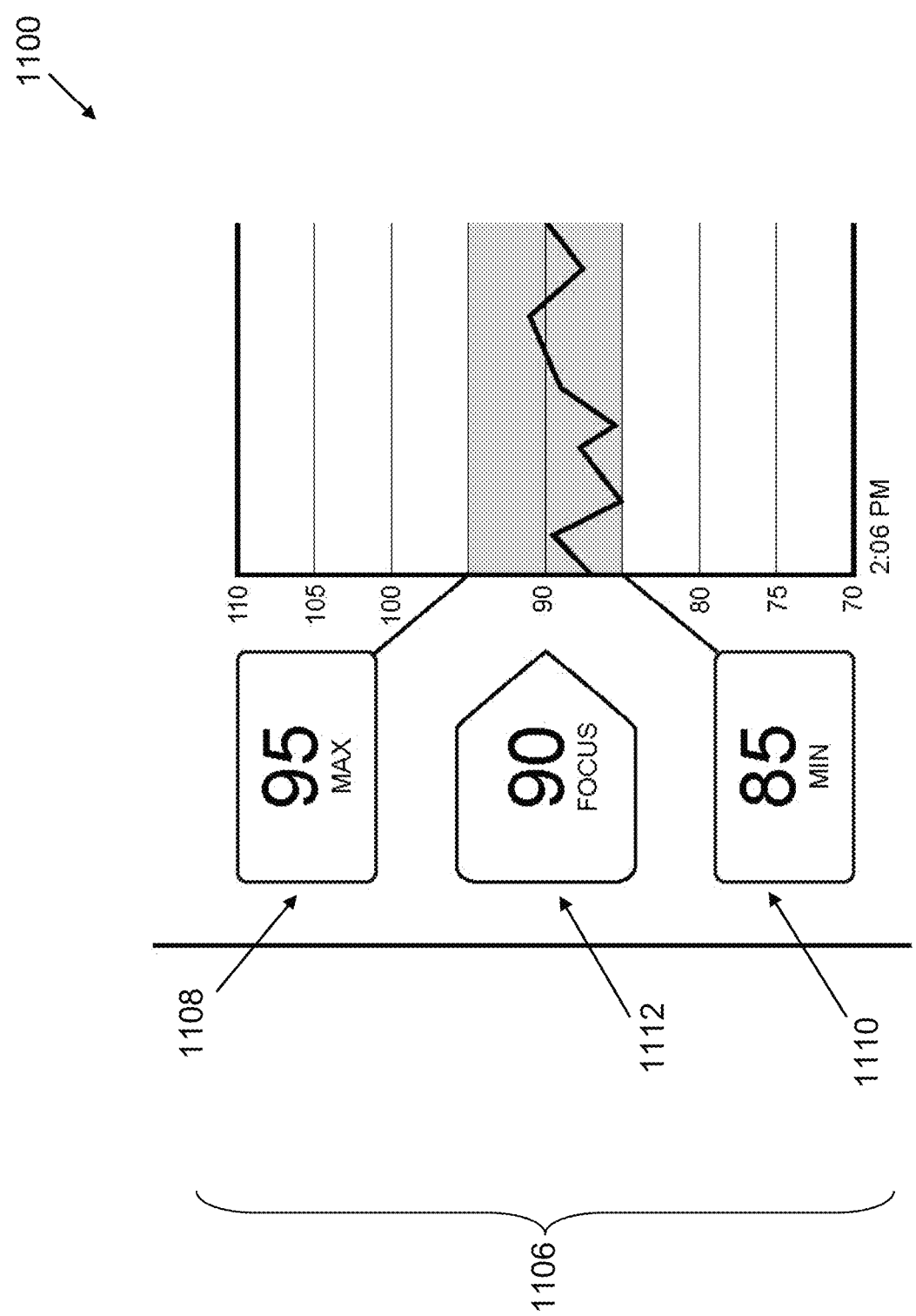
FIG. 12 illustrates an enlarged portion of the GUI of FIG. 11.

FIG. 12 illustrate an enlarged view of a portion of the GUI 1100 presenting a predetermined or preferred range 1106 of the vital sign of the patient, which can be defined by a minimum value 1110 and a maximum value 1108. The GUI 1100 may also include a focus value 1112 for the vital sign which, like the predetermined range 1106, can be set and/or changed by the clinician or other medical professional. The focus value 1112 can be used with an algorithm to determine a dosage rate of the medication based on the patient's information, such as described above.

The GUI 1100 shown in FIG. 11 can further display or present the predetermined or preferred range 1106 of the vital sign of the patient, which, as discussed above, can be defined by a minimum value 1110 and a maximum value 1108. In some embodiments, it is contemplated that the vital sign values that fall within the predetermined range 1106 may be shown in a first color and the vital sign values that fall outside of the predetermined range 1106 may be shown in a different color. In this manner, a clinician or other medical professional can quickly see where the patient's vital sign has fallen outside of the range 1106.

The GUI 1100 may also include a focus value 1112 for the vital sign which, like the predetermined range 1106, can be set and/or changed by the clinician or other medical professional. The focus value 1112 can be used with an algorithm to determine a dosage rate of the medication based on the patient's information, such as described in co-pending U.S. patent application having Ser. No. 17/365,730 filed on Jul. 1, 2021.

As new vital signs are received from the first source, it is contemplated that the latest vital sign can be presented as the current vital sign 1114 and the prior vital sign can be saved to the historical data.

As shown, the historical data of the vital sign is preferably plotted or graphed on the GUI 1100 for quick review of the vital sign information 1102. In this manner, the historical data can depict the vital sign information 1102 of the patient over an elapsed time period. It is contemplated that the specific time period of historical data shown can be changed by the clinician or other medical professional by selecting a time period object on the GUI 1100. Selecting the object can open a pop-up window or other interface to select the new time period, such as described above.

A time in target percentage 1116 or another indicator can also be displayed on the GUI 1100. As discussed above, this time in target value 1116 represents the percentage of time the patient's vital sign has remained within the predetermined range 1106. To calculate the time in target value 1116, a first set of vital signs can be generated by selecting items of the historical data falling within a predefined time period, which may match the elapsed time period of historical vital sign information shown on the GUI 1100. An amount of time that the first set of vital signs were within the predetermined range 1106 can be determined or estimated, and the amount of time is divided by the predefined time period. As shown in FIG. 11, the time in target value 1116 (e.g., 90%) is presented for the automated management of the patient's vital sign. Such value 1116 advantageously allows the clinician to quickly understand how often the patient's vital sign was maintained within the predetermined range 1106.

The GUI 1100 can comprise various other objects to allow for setting of the minimum value 1110 and the maximum value 1108, as well as the focus value 1112. For example, it is contemplated that the minimum value 1110, the maximum value 1108, and the focus value 1112 can each be, or collectively can be, a selectable object, and once selected a pop-up window or other change to the GUI 1100 can be presented (such as the interface 2100 in FIG. 21) that allows one or more of the minimum value 1110, the maximum value 1108, and the focus value 1112 to be adjusted. Alternatively, it is contemplated that a specific area about the values can be selectable, such as described above.

As shown in FIG. 11, the GUI 1100 can further display information 1104 concerning a dosage rate of a medication being administered to the patient. For example, a current dosage rate 1118 of the medication can be displayed as well as a minimum dosage rate 1122 and a maximum dosage rate 1120 of the medication. The minimum dosage rate 1122 and the maximum dosage rate 1120 can be selected by selecting a dosage rate object on the GUI, which can generate a pop-up or other interface for changing one or both of the minimum dosage rate 1122 and the maximum dosage rate 1120. For example, it is contemplated that the minimum dosage rate 1122 and the maximum dosage rate 1120 can each be, or collectively can be, a selectable object, and once selected a pop-up window or other change to the GUI 1100 can be presented that allows one or more of the values to be adjusted. Alternatively, it is contemplated that a specific area about the values can be selectable, such as described above.

As shown in FIG. 11, it is contemplated that the current dosage rate 1118 and historical dosage rates of the medication can be plotted/graphed or otherwise presented on the GUI 1100 for an elapsed time period. This advantageously allows the clinician or other medical professional to quickly be apprised of changes to the dosage rate over time, and whether the dosage rate has significantly increased or decreased despite the patient's vital sign remaining within the predetermined range 1106. It is contemplated that the specific time period of historical data shown can be changed by the clinician or other medical professional by selecting a time period object on the GUI 1100. Selecting the object can open a pop-up window or other interface to select the new time period, such as described above.

In some embodiment, a dosage change indicator 1124 can be generated and presented on the GUI 1100, which is shown next to the current dosage rate 1118, for example. The dosage change indicator 1124 represents a trend line between the current dosage rate and historical data, and may show the dosage rate has changed slightly, drastically, or not at all, as well as the general direction (e.g., increase or decrease of the dosage rate). As shown, the dosage change indicator 1124 may be represented visually by one or more arrows, but could be represented by other shapes or objects, colors, or otherwise.

Such an indicator may also be displayed for the vital sign information 1102, such as to show how the vital sign is changing over time.

In some embodiments, it is contemplated that the GUI 1100 may also present a remaining amount of medication, which can be estimated as a function of an initial volume of medication, the current dosage rate, and any historical dosage rate data, and the estimated remaining amount of medication can be presented on the GUI 1100.

As shown in FIG. 11, an automated/manual management object 1126 can be presented on the GUI 1100, which can allow the system to switch from a closed-loop automated system for managing the vital sign and the current dosage rate to a manual system by selecting the object 1126. In some embodiments, upon selecting the automated/manual management object 1126, a new interface or pop-up window can be presented to allow the system's mode to be changed, such as described above.

Figure 13:
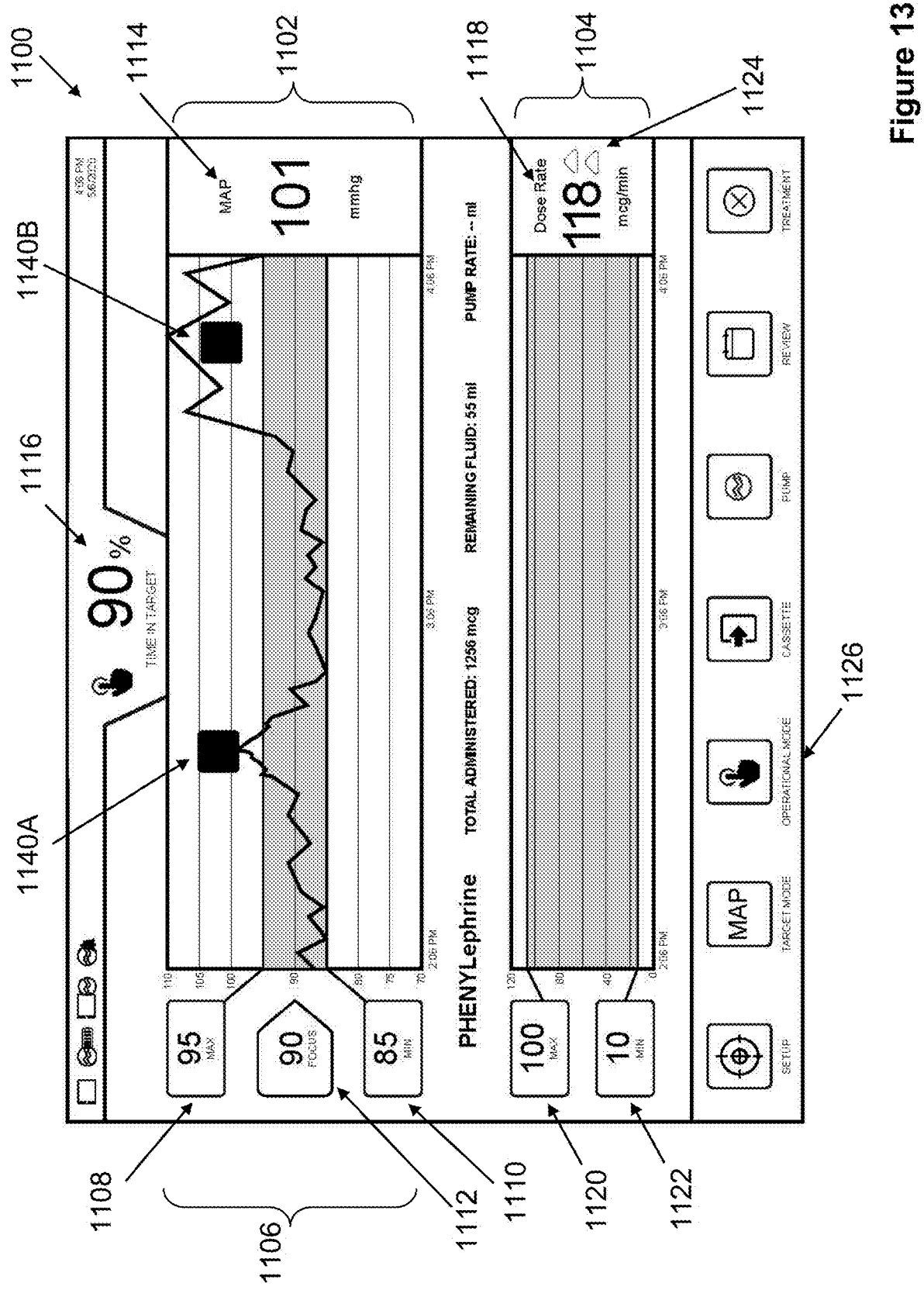
FIG. 13 illustrates another embodiment of an exemplary GUI presented on a display screen.

As shown in FIG. 13, the GUI 1100 may further comprise one or more indicator objects 1140A, 1140B that may be presented on the chart/graph of historical data of the vital sign 1102 at specific points in time. Thus, for example, a first indicator object 1140A may be presented on the chart of historical data at a specific time between 2:06 pm and 3:06 pm, and a second indicator object 1140B is presented on the chart of historical data at a specific time between 3:06 pm and 4:06 pm. It is preferred that the specific position of the one or more indicator objects 1140A, 1140B is related to a time that a notable event occurred. Such event could include, for example, a specific time when an anomaly or danger was detected, a specific time information was received that triggered an alarm/alert, or a change or alert relative to a second vital sign of the patient being monitored.

Although two indicator objects 1140A, 1140B are shown, it is contemplated that the number of indicator objects on the GUI 1100 will correspond to the number of specific alerts or other information to be presented. Furthermore, it is contemplated that each of the indicator objects 1140A, 1140B will remain associated to the specific time on the chart. Thus, as the chart of historical data updates to show a time period for a different elapsed time, the indicator objects 1140A, 1140B will move to the left until they are no longer shown or they are presented in a different manner, for example.

Figure 14:
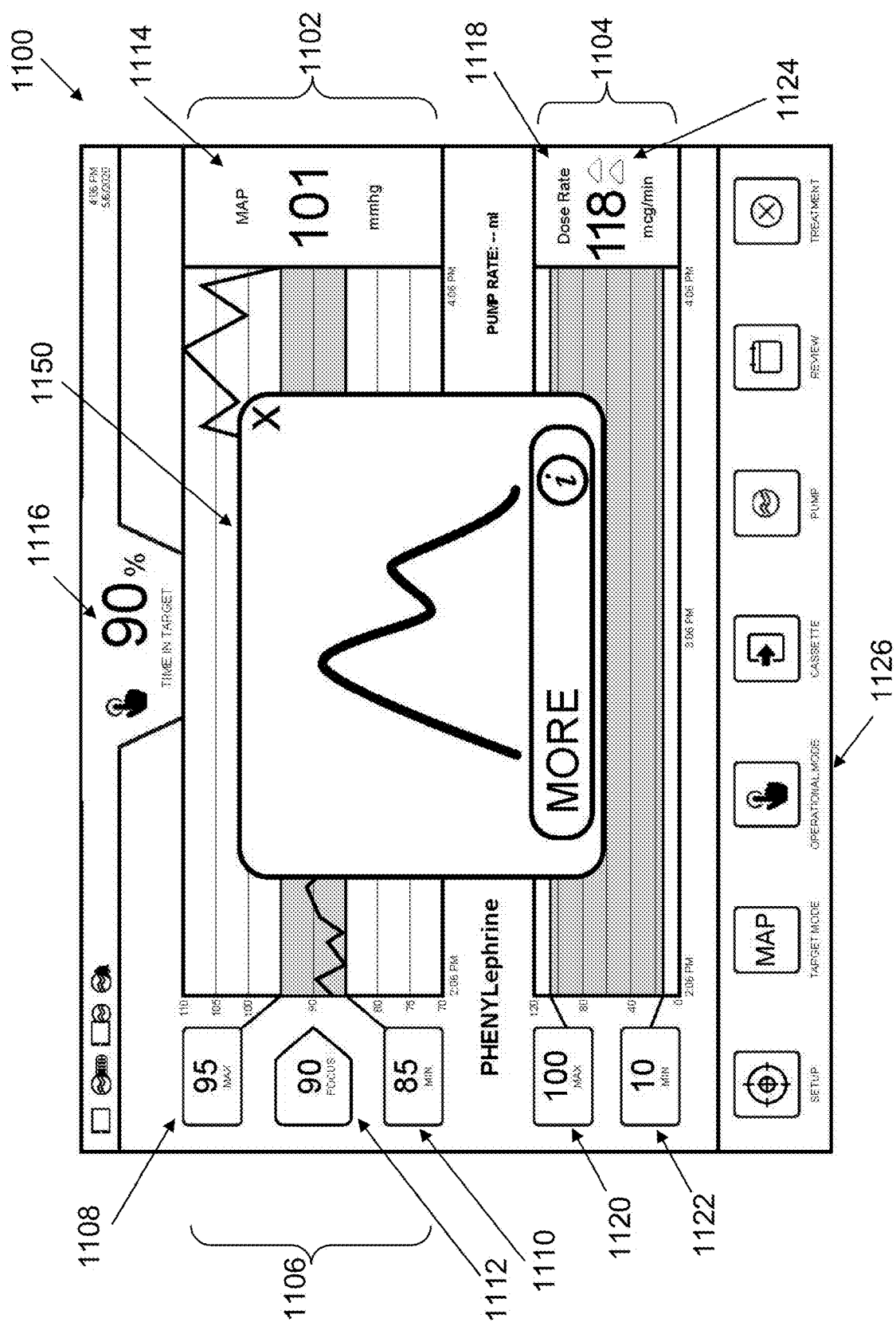
FIG. 14 illustrates the GUI of FIG. 13 with a window overlaid on the GUI.

Preferably, each of the indicator objects 1140A, 1140B comprises a selectable object that can be clicked on or otherwise selected by a clinician or other medical professional. As shown in FIG. 14, it is contemplated that upon selection of the first indicator object 1140A, for example, a first window 1150 may be overlayed on the GUI 1100 with the first window 1150 containing a first set of information related to the object 1140A. The first set of information could comprise various information related to the patient and/or the patient's care. As shown in FIG. 14, the first information may concern an irregular heartbeat of the patient detected at the specific time where the indicator object 1140A was displayed on the chart. Alternatively, such information may include, for example, a blood oxygen saturation level of the patient, a body temperature of the patient, a second vital sign of the patient, a change in dosage rate of the medication, a change in dosage rate of a second medication, and so forth.

It is especially preferred that the first information contains or concerns information not otherwise reported on the GUI 1100. In this manner, the clinician or other medical professional can be alerted to pertinent information about the patient but that may not be routinely presented on the GUI 1100 along with the patient's vital sign and dosage rate of the medication being administered.

With respect to the remaining numerals in each of FIGS. 13 and 14, the same considerations for like components with like numerals of FIG. 1A apply.

Figure 15:
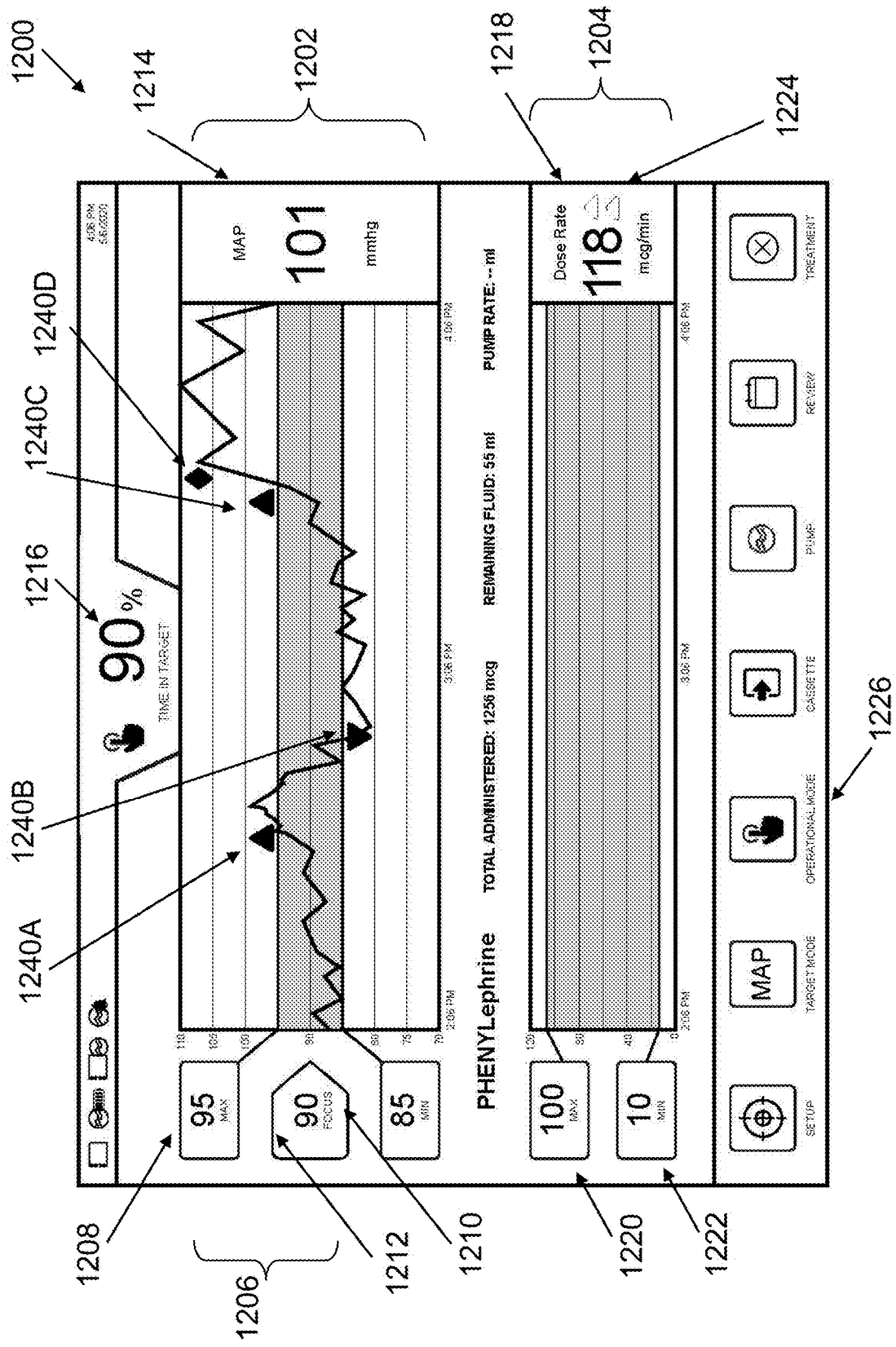
FIG. 15 illustrates another embodiment of an exemplary GUI presented on a display screen.
Figure 16:
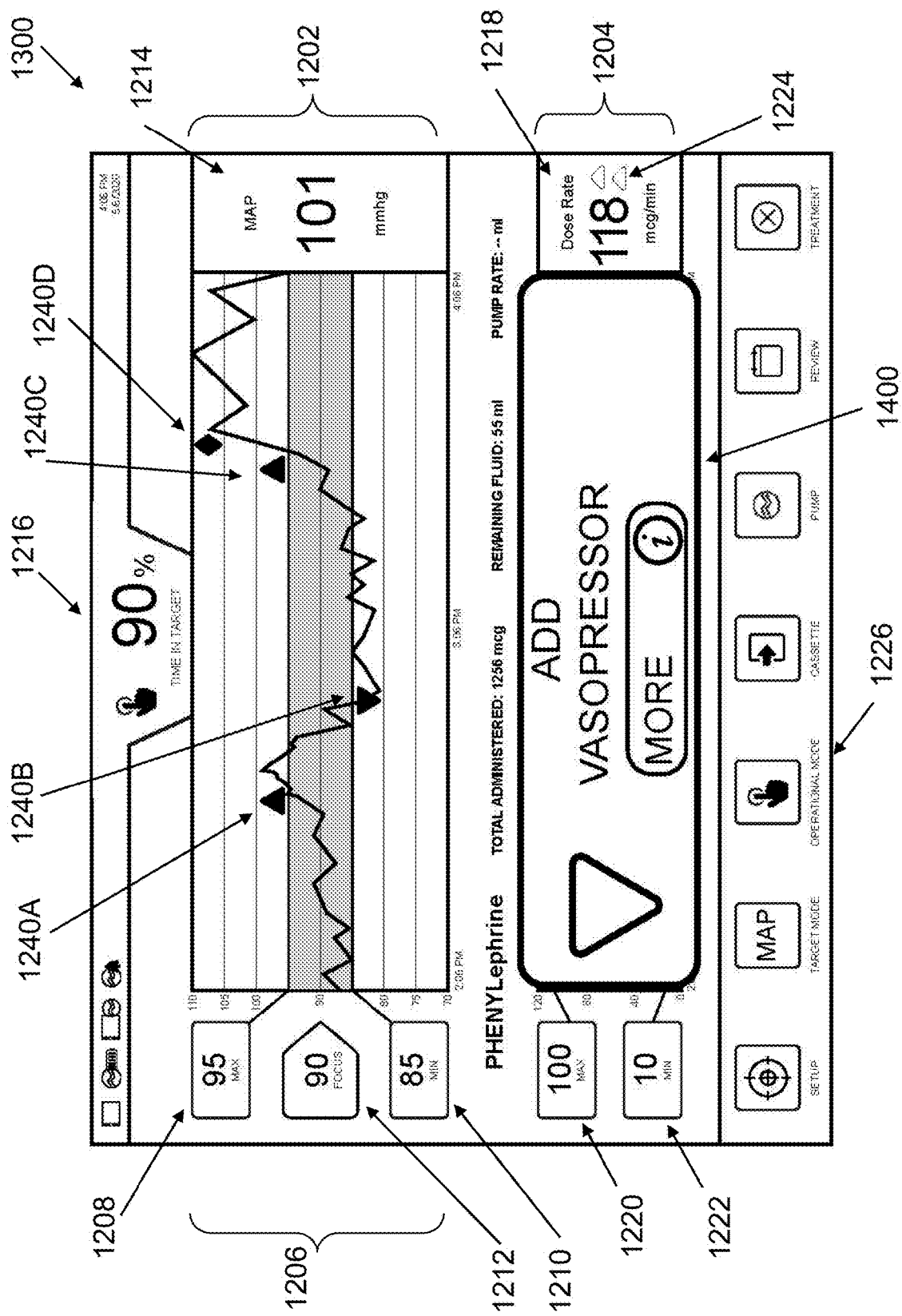
FIG. 16 illustrates the GUI of FIG. 15 with a window overlaid on the GUI.
Figure 17:
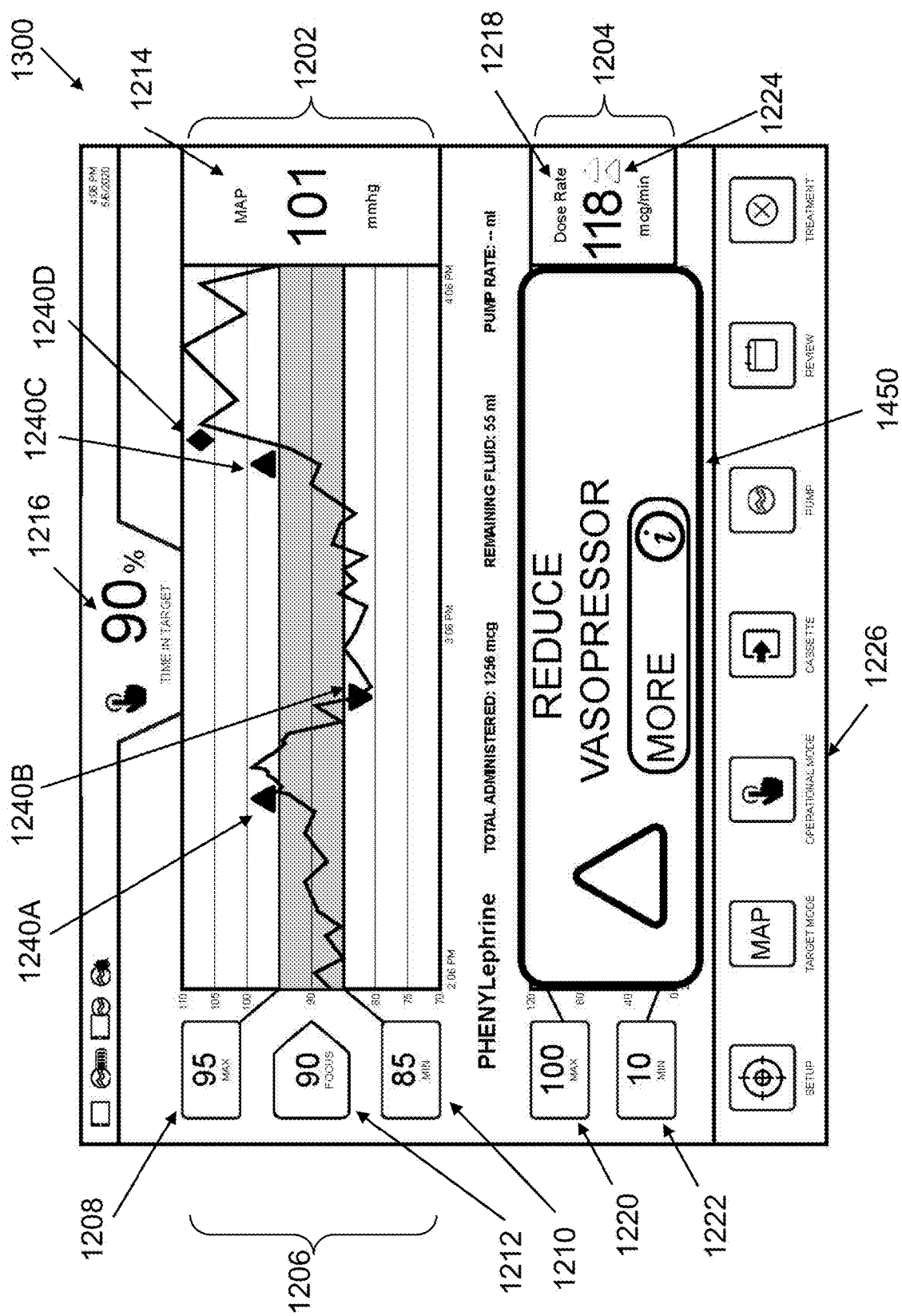
FIG. 17 illustrates the GUI of FIG. 15 with a different window overlaid on the GUI.

FIGS. 15-17 illustrate another embodiment of a GUI 1200 for monitoring a vital sign of a patient, similar to that described above with respect to FIG. 11. As shown in FIG. 15, one or more indicator objects 1240A-1240D can be presented on the chart/graph of historical data of the vital sign 1202 at specific points in time. It is contemplated that one or more features (e.g., orientation, size, color, shape, etc.) of each of the indicator objects 1240A-1240D can be varied to visually indicate different information. For example, indicator object 1240A is represented by an upwardly pointing arrow and may indicate a status that is different from indicator object 1240B (represented by a downwardly pointing arrow), although the subject matter may overlap. While indicator object 1240C (represented by an upwardly pointing arrow) may indicate similar information to indicator object 1240A, as the symbols are the same shape and orientation. In contrast, indicator object 1240D may indicate a status and subject matter that is entirely different from indicator objects 1240A-1240C, hence a different shape.

As discussed above, it is preferred that the specific position of the one or more indicator objects 1240A-1240D may be related to why the object was created. This could be, for example, a specific time when an anomaly or danger was detected, or information was received at that time which triggered an alarm/alert. Although four indicator objects are shown, it is contemplated that the number of indicator objects on the GUI 1200 will be based on the specific alerts or other information to be presented. Furthermore, it is contemplated that each of the indicator objects 1240A-1240D will remain associated to the specific time on the chart. Thus, as the chart updates to show a different time period, the indicator objects will move to the left until they are no longer shown or they are presented in a different manner, for example.

Preferably, each of the indicator objects 1240A-1240D may comprise a selectable object that can be clicked on or otherwise selected by a clinician or other medical professional. As shown in FIG. 16, for example, it is contemplated that upon selection of the second indicator object 1240B, a first window 1400 can be overlayed on the GUI 1300 with the first window 1400 containing a first set of information. Here, the first set of information concerns a change in a dosage rate of a medication of the patient at the specific time where the indicator object 1240B is presented on the chart. As shown in FIG. 17, upon selection of the first indicator object 1240A, a second window 1450 can be overlayed on the GUI 1300 with the second window 1450 containing a second set of information. Here, the second information concerns a different change in dosage rate of the medication at the specific time where the first indicator object 1240A is presented on the chart.

Figure 18:
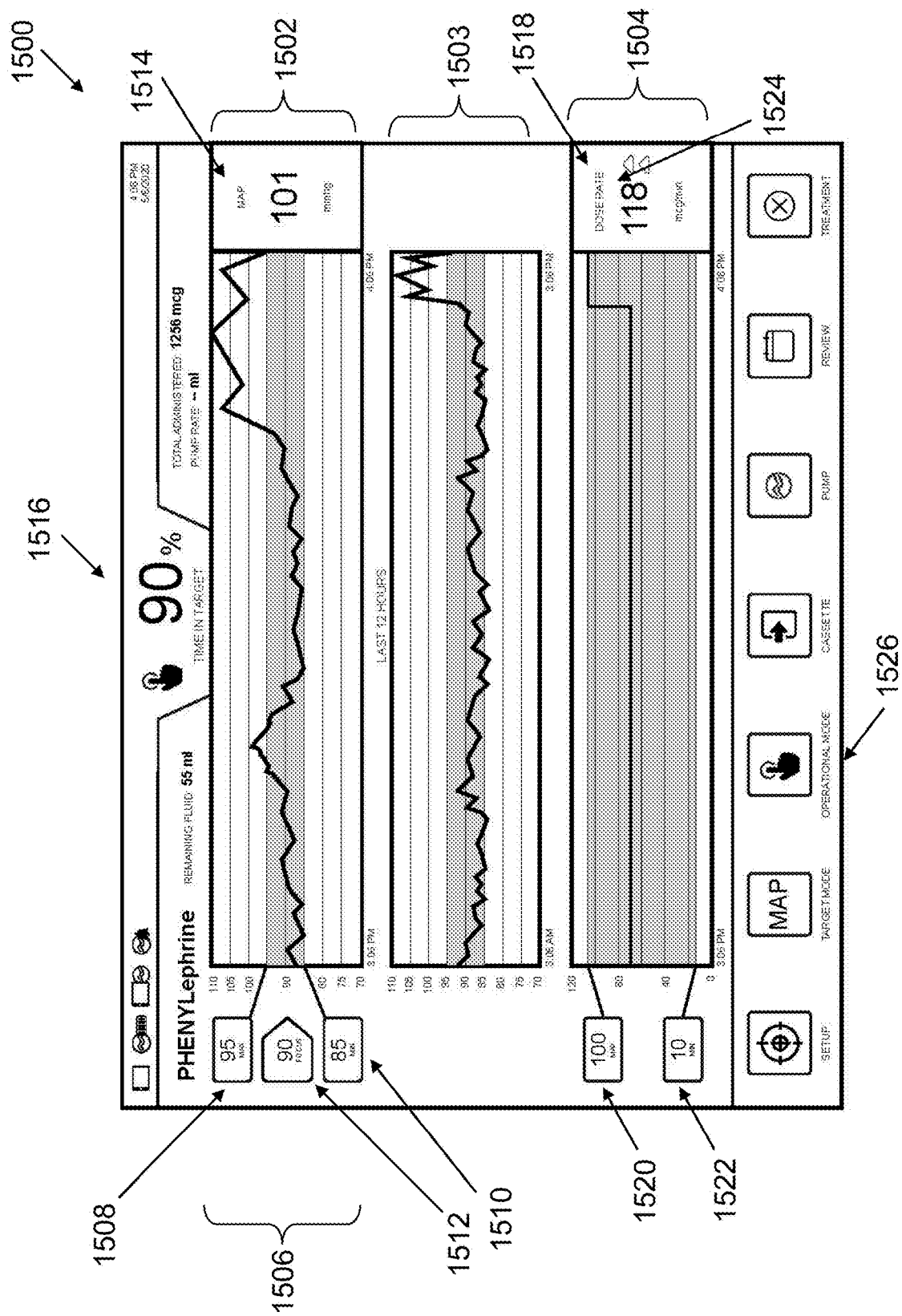
FIG. 18 illustrates another embodiment of an exemplary GUI presented on a display screen.

FIG. 18 illustrates another embodiment of a GUI 1500 that can be presented on a display screen, for example, for monitoring a vital sign and/or dosage rate of a medication being administered to a patient. The GUI 1500 can display vital sign information 1502 of a patient and dosage rate information 1504 being administered to a patient. The vital sign information 1502 may include, for example, a current vital sign of the patient received from a first source as well as a chart/graph of historical data relating to the patient's vital sign based on prior information received from the first source. The GUI 1500 can further display or present a predetermined or preferred range 1506 of the vital sign of the patient, which can be defined by a minimum value 1510 and a maximum value 1508. In some embodiments, it is contemplated that the vital sign values that fall within the predetermined range 1506 can be shown in a first color and the vital sign values that fall outside of the predetermined range 1506 can be shown in a different color. In this manner, a clinician or other medical professional can quickly see when the patient's vital sign has fallen outside of the range 1506.

The GUI 1500 may also include a focus value 1512 for the vital sign which, like the predetermined range 1506, can be set and/or changed by the clinician or other medical professional. The focus value 1512 can be used with an algorithm to determine a dosage rate of the medication based on the patient's information, such as described in co-pending U.S. patent application having Ser. No. 17/365,730 filed on Jul. 1, 2021.

As new vital signs are received from the first source, it is contemplated that the latest vital sign can be presented as the current vital sign 1514 and the prior vital sign can be saved to the historical data.

As shown, the historical data of the vital sign is preferably plotted or graphed on the GUI 1500 for quick review of the vital sign information 1502. In this manner, the historical data can depict the vital sign information 1502 of the patient over an elapsed time period. It is contemplated that the specific time period of historical data shown can be changed by the clinician or other medical professional by selecting a time period object on the GUI 1500. Selecting the object can open a pop-up window or other present a revised interface to select the new time period, such as described above.

As shown in FIG. 18, it is contemplated that in addition to the historical data shown for vital sign information 1502 over the elapsed time period, the GUI 1500 may also present historical data of the vital sign for a second elapsed time period 1503, which may be longer or shorter than the elapsed time period. As shown, the second elapsed time period is twelve hours while the first elapsed time period is one hour. These time periods could be changed as desired.

As discussed above, a time in target percentage 1516 or another indicator can also be displayed on the GUI 1500.

With respect to the remaining numerals in FIG. 18, the same considerations for like components with like numerals of FIG. 1A apply.

Figure 19:
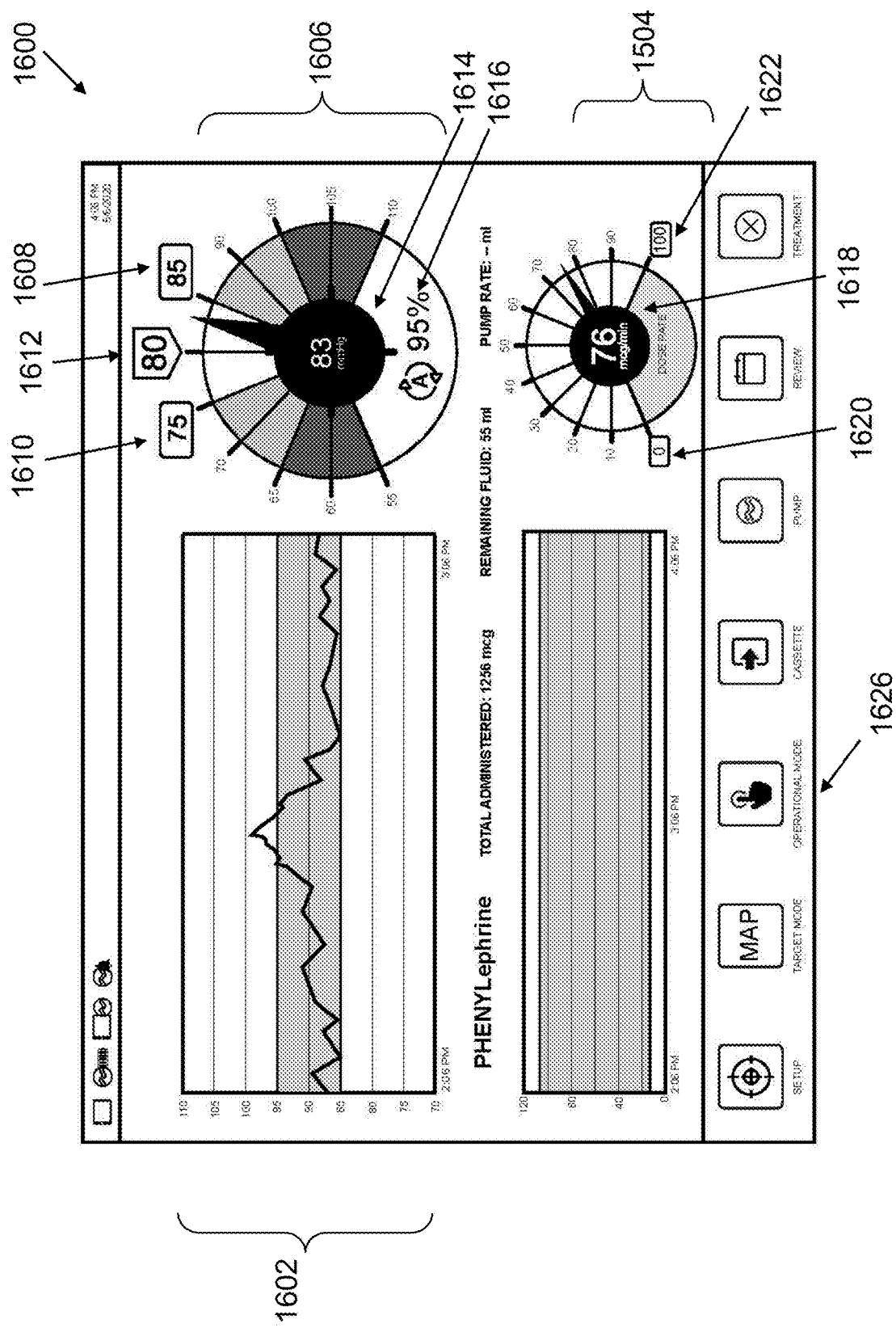
FIG. 19 illustrates another embodiment of an exemplary GUI presented on a display screen.

FIG. 19 illustrates another embodiment of a GUI 1600 that can be presented on a display screen, for example, for monitoring a vital sign of a patient and/or a dosage rate of a medication being administered to a patient. The GUI 1600 can display vital sign information 1602 and dosage rate information 1604 for a patient. The vital sign information 1602 may include, for example, a current vital sign of the patient received from a first source as well as a chart of historical data relating to the patient's vital sign based on prior information received from the first source.

The GUI 1600 may further display or present a predetermined or preferred range 1606 of the vital sign of the patient, shown as a dial on the upper right corner of the GUI 1600, for example. The predetermined range 1606 can be defined by a minimum value 1610 and a maximum value 1608. The GUI 1600 may also include a focus value 1612 for the vital sign which, like the predetermined range 1606, can be set and/or changed by the clinician or other medical professional. Similar to a speedometer, the dial of the GUI 1600 can visually indicate the current vital sign 1614 with respect to the predetermined range 1606. In this manner, a clinician or other medical professional can quickly ascertain if a patient's vital sign has fallen outside of the predetermined range 1606.

In such embodiment, it is contemplated that a time in target value 1616, such as described above, can be displayed adjacent to the visual indicator of the predetermined range 1606. With respect to the remaining numerals in FIG. 19, the same considerations for like components with like numerals of FIG. 1A apply.

Figure 20:
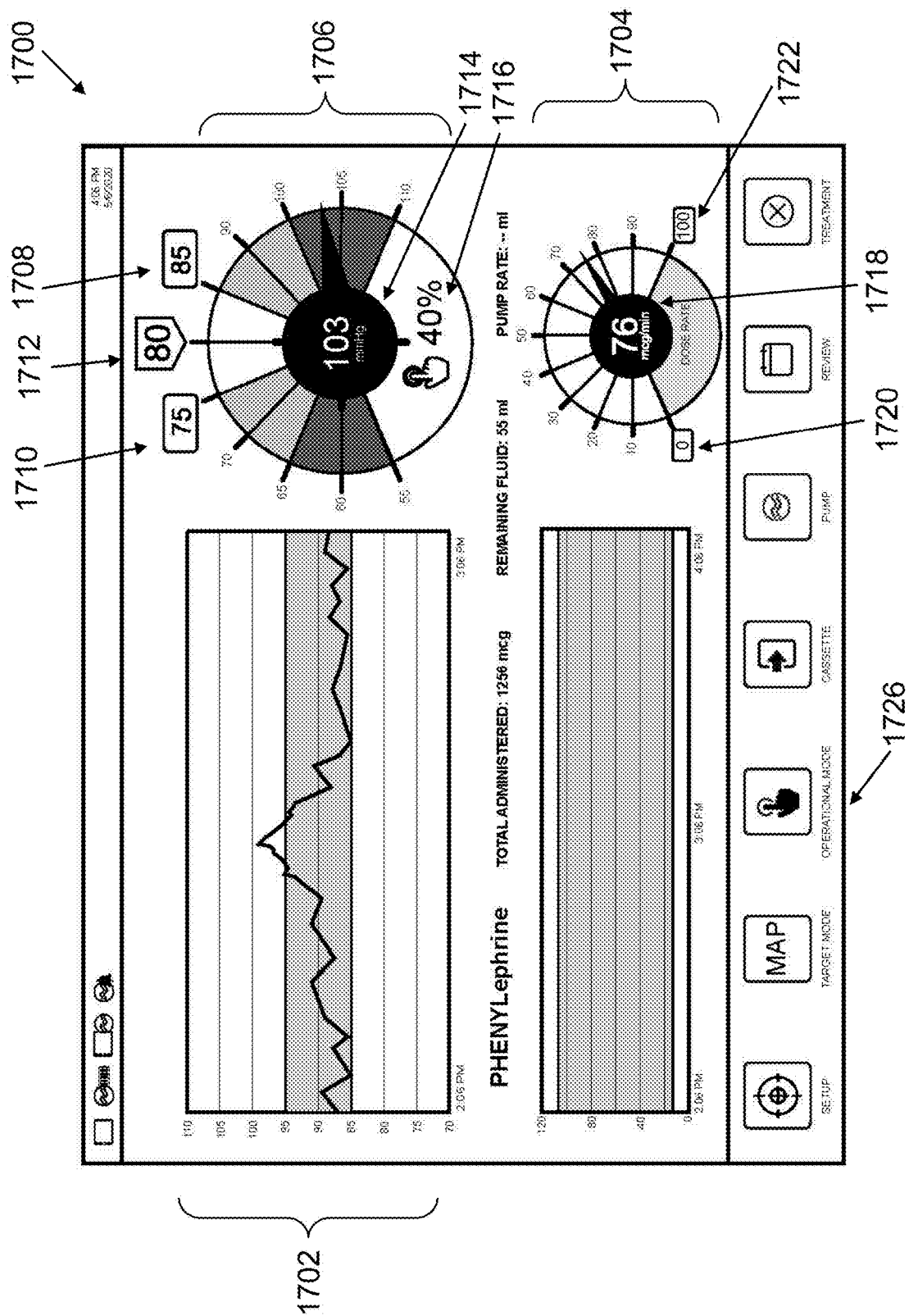
FIG. 20 illustrates another embodiment of an exemplary GUI presented on a display screen.

FIG. 20 illustrates another embodiment of a GUI 1700 that can be presented on a display screen, for example, for monitoring a vital sign of a patient and/or a dosage rate of a medication being administered to a patient. The GUI 1700 can display vital sign information 1702 and dosage rate information 1704 for a patient. The vital sign information 1702 may include, for example, a current vital sign of the patient received from a first source as well as a chart of historical data relating to the patient's vital sign based on prior information received from the first source.

The GUI 1700 can further display or present a predetermined or preferred range 1706 of the vital sign of the patient, shown as a dial on the upper right corner of the GUI 1700, for example. The predetermined range 1706 can be defined by a minimum value 1710 and a maximum value 1708. The GUI 1700 may also include a focus value 1712 for the vital sign which, like the predetermined range 1706, can be set and/or changed by the clinician or other medical professional. Similar to a speedometer, the dial of the GUI 1700 can visually indicate the current vital sign 1714 with respect to the predetermined range 1706. In this manner, a clinician or other medical professional can quickly ascertain if the patient's vital sign has fallen outside of the predetermined range 1706.

In such embodiment, it is contemplated that a time in target value 1716, such as described above, can be displayed adjacent to the visual indicator of the range 1706.

As shown in FIG. 20, the GUI 1700 may also display information 1704 concerning a dosage rate of a medication being administered to the patient as a visual dial or meter. For example, a current dosage rate 1718 of the medication being administered can be displayed as well as a preset minimum dosage rate 1722 and maximum dosage rate 1720 of the medication. The visual indication advantageously allows the clinician or other medical professional to quickly be apprised of where the dosage rate falls with respect to the minimum dosage rate 1722 and a maximum dosage rate 1720.

With respect to the remaining numerals in FIG. 20, the same considerations for like components with like numerals of FIG. 1A apply.

Figure 21:
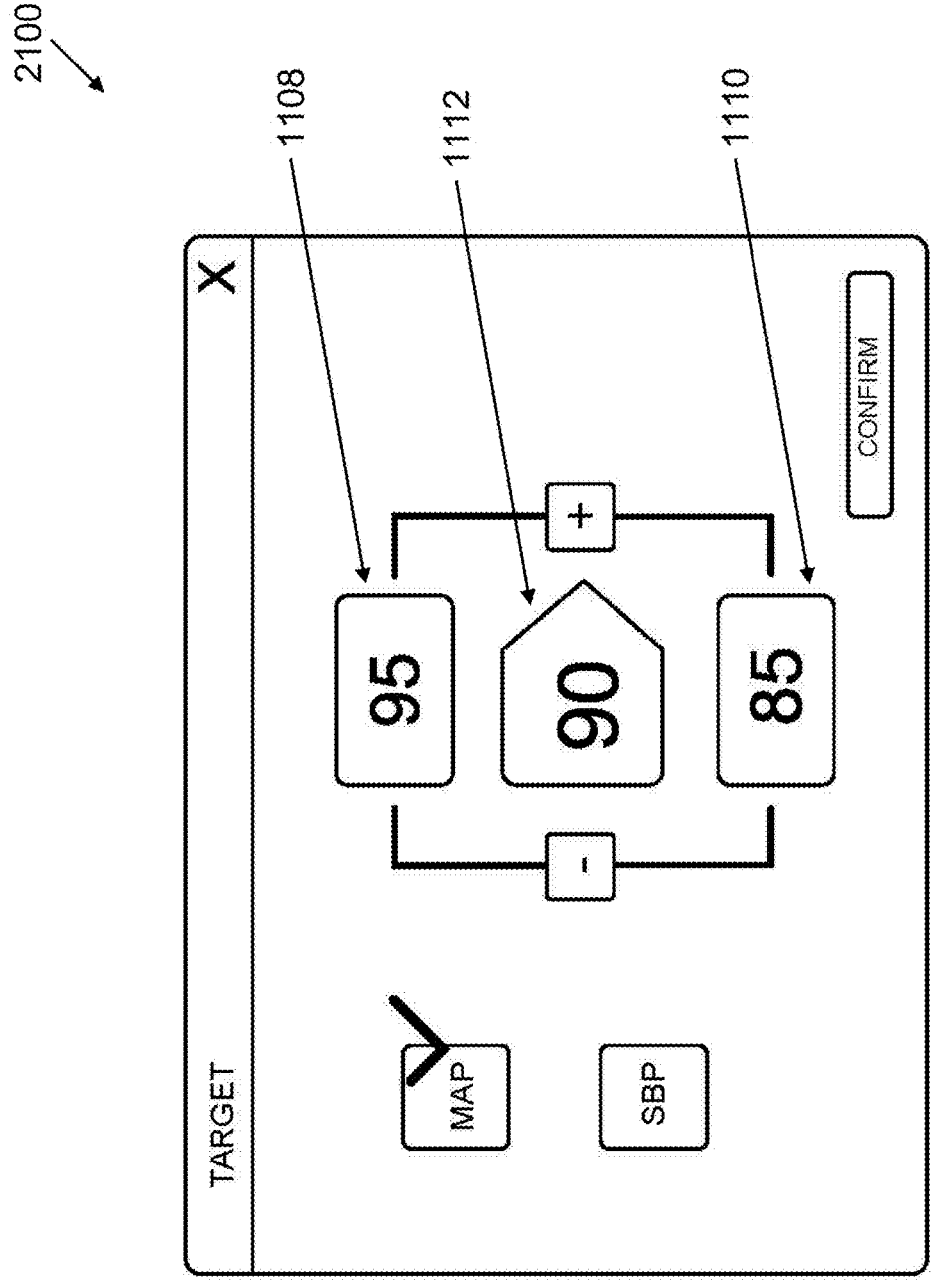
FIG. 21 illustrates another embodiment of an exemplary GUI for adjusting a predetermined range for a vital sign.

FIG. 21 illustrates another embodiment of a GUI 2100 which may be a pop-up window or other interface that allows a clinician or other medical professional to adjust a predefined target range of values of a vital sign (e.g., a minimum value of range 1110 and a maximum value of range 1108) and a focus value 1112 of a vital sign of a patient. The GUI 2100 may also be used to change a vital sign between a mean arterial pressure (MAP) and a standard blood pressure (SBP) where a patient's blood pressure is being monitored.

Figure 22A:
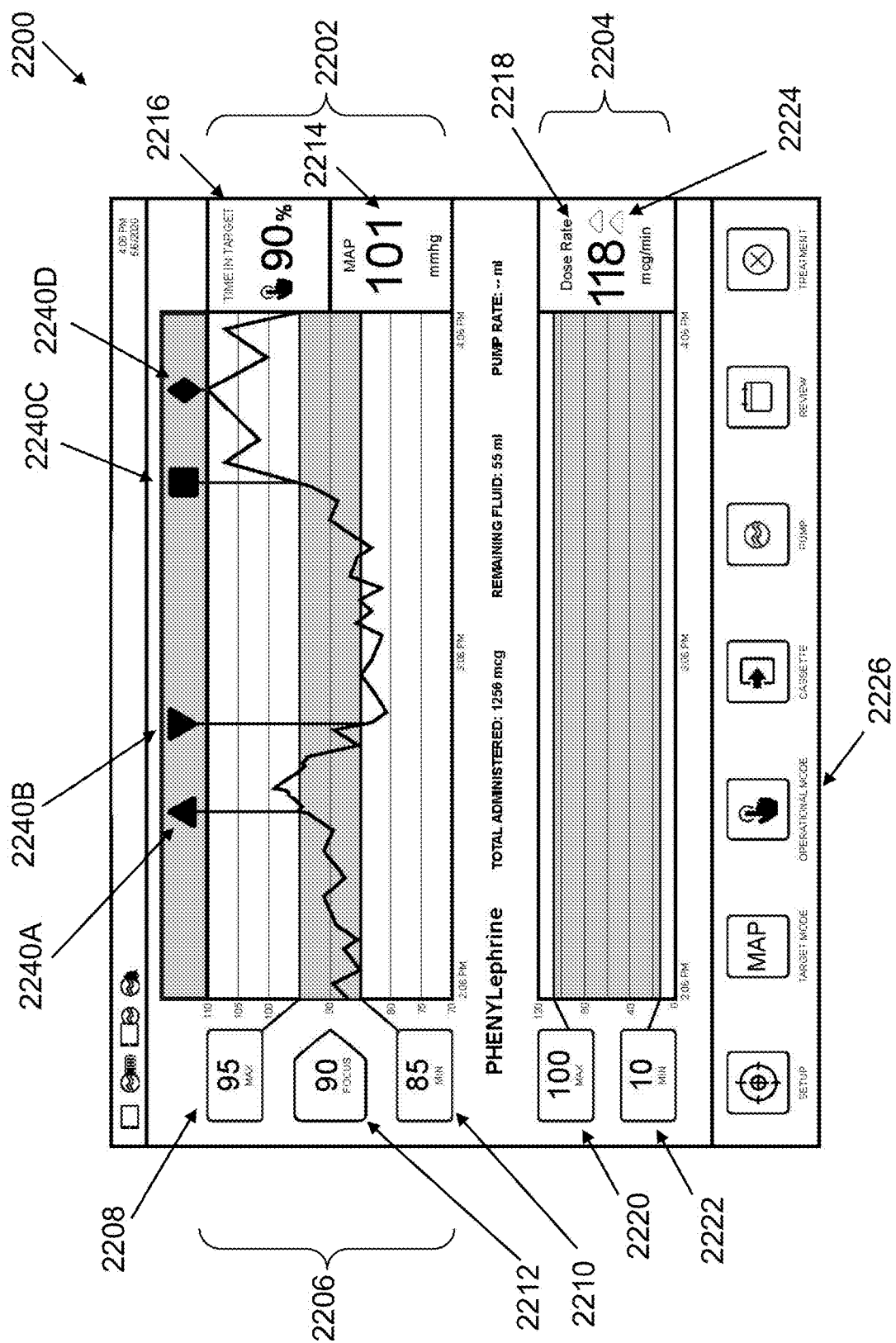
FIG. 22A illustrates another embodiment of an exemplary GUI presented on a display screen.
Figure 22B:
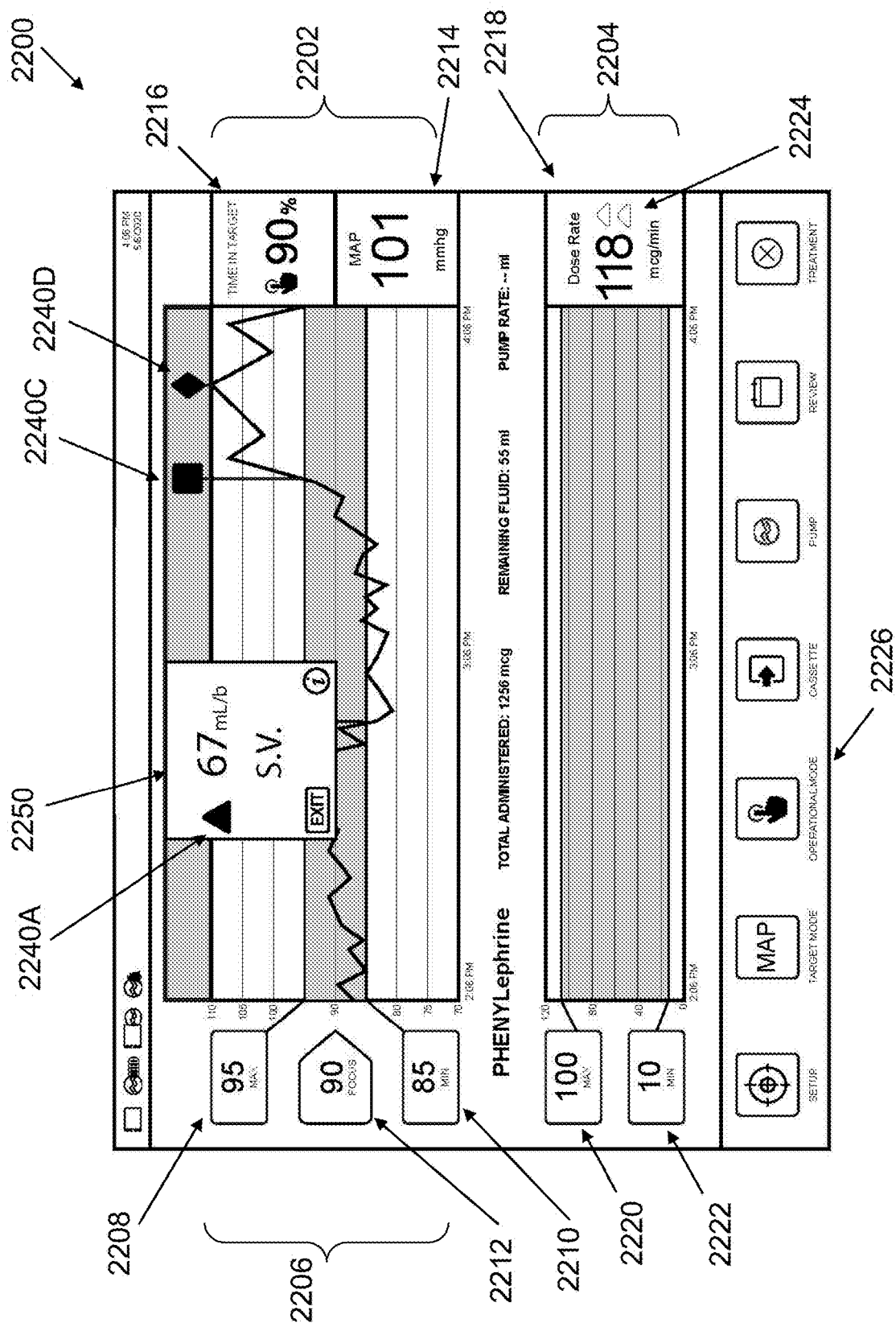
FIG. 22B illustrates the GUI of FIG. 22A with a window overlaid on the GUI.
Figure 22C:
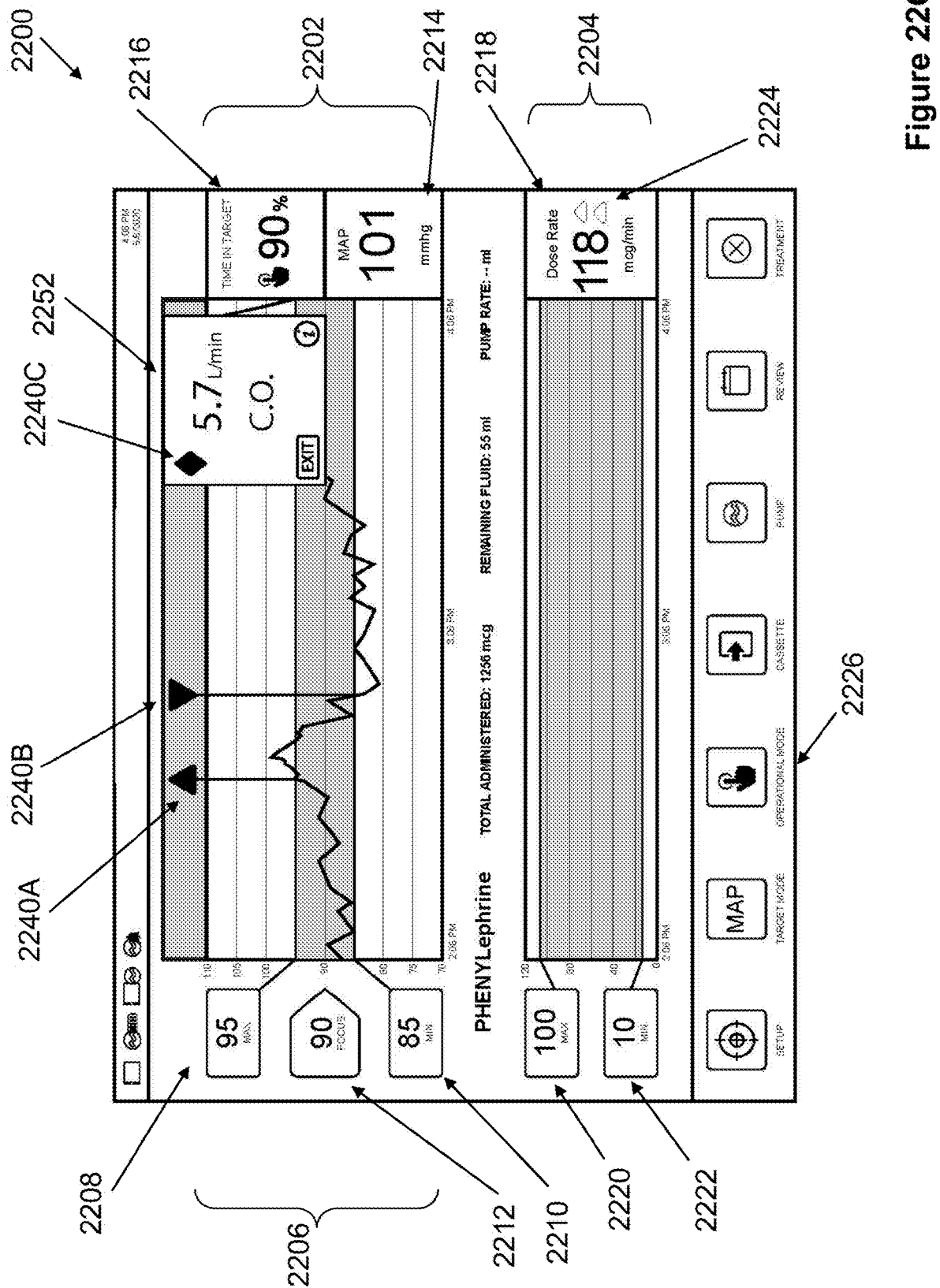
FIG. 22C illustrates the GUI of FIG. 22A with a window overlaid on the GUI.

FIGS. 22A-22C illustrate another embodiment of a GUI 2200 for monitoring one or more vital signs of a patient that may be presented on a display screen of a device, for example. The GUI 2200 can display a patient's vital sign information 2202 and dosage rate information 2204 of a medication being administered to the patient. The vital sign information 2202 may include, for example, a current vital sign of the patient received from a first source as well as historical data relating to the patient's vital sign based on prior information received from the first source. As new vital signs are received from the first source, it is contemplated that the latest vital sign can be presented as the current vital sign 2214 and the prior vital sign can be saved to the historical data and presented on the GUI 2200.

The GUI 2200 can further display or present a predetermined or preferred range 2206 of the vital sign of the patient, which may be defined by a minimum value 2210 and a maximum value 2208. In some embodiments, it is contemplated that the vital sign values of the patient that fall within the predetermined range 2206 can be shown in a first color and the vital sign values of the patient that fall outside of the predetermined range 2206 can be shown in a different color. In this manner, a clinician or other medical professional can quickly see at which times and for how long the patient's vital sign has fallen outside of the range 2206.

The GUI 2200 may also include a focus value 2212 for the vital sign which, like the predetermined range 2206, can be set and/or changed by the clinician or other medical professional. It is contemplated that the focus value 2212 can be used with an algorithm to determine a dosage rate of the medication based on the patient's information, such as described above.

As shown, the historical data of the vital sign is preferably plotted or graphed on the GUI 2200 for quick review of the patient's vital sign information 2202. In this manner, the historical data can depict the patient's vital sign information 2202 over an elapsed time period. It is contemplated that the specific time period of historical data shown can be changed by the clinician or other medical professional by selecting a time period object on the GUI 2200. Selecting the object can open a pop-up window or other present a revised interface to select the new time period. An exemplary embodiment of such an interface 400 is shown in FIG. 4.

A time in target percentage 2216 or another indicator can also be displayed on the GUI 2200. This time in target value 2216 represents the percentage of time the patient's vital sign has remained within the predetermined range 2206 during the time period shown on the GUI 2200 or other set time period. To calculate the time in target value 2216, a first set of vital signs can be generated by selecting items of the historical data falling within a predefined time period, which may match the elapsed time period of historical vital sign information shown on the GUI 2200. An amount of time that the first set of vital signs were within the predetermined range 2206 can be determined or estimated, and the amount of time is divided by the predefined time period. The target value 2216 advantageously allows the clinician to quickly understand the percentage of time the patient's vital sign was maintained within the predetermined range 2206.

The GUI 2200 can further display information 2204 concerning a dosage of medication being administered to the patient. For example, a current dosage rate 2218 of the medication being administered can be displayed as well as a minimum dosage rate 2222 and a maximum dosage rate 2220 of the medication. The minimum dosage rate 2222 and the maximum dosage rate 2220 can be selected by selecting a dosage rate object on the GUI 2200, which can generate a pop-up or other interface for changing one or both of the minimum dosage rate 2222 and the maximum dosage rate 2220. For example, it is contemplated that the minimum dosage rate 2222 and the maximum dosage rate 2220 can each be, or collectively can be, a selectable object, and once selected a pop-up window or other change to the GUI 2200 can be presented that allows one or more of the values to be adjusted. Alternatively, it is contemplated that a specific area about the values can be selectable. FIG. 3 illustrates one embodiment of an interface 300 that can be presented when an object is selected to vary the minimum dosage rate 2222 and/or the maximum dosage rate 2220.

Preferably, the current dosage rate 2218 and historical dosage rates of the medication being administered can be plotted, graphed, or otherwise presented on the GUI 2200 for an elapsed time period. This advantageously allows the clinician or other medical professional to quickly be apprised of changes to the dosage rate over time, and whether the dosage rate has significantly increased or decreased despite the patient's vital sign remaining within the predetermined range 2204. It is contemplated that the specific time period of historical data shown can be changed by the clinician or other medical professional by selecting a time period object on the GUI 2200. Selecting the object can open a pop-up window or other present a revised interface to select the new time period. An exemplary embodiment of such an interface 400 is shown in FIG. 4.

A dosage change indicator 2224 can be presented on the GUI 2200, which is shown next to the current dosage rate 2218. The dosage change indicator 2224 represents a trend line between the current dosage rate of the medication and historical data and may show that the dosage rate has changed slightly, drastically, or not at all, as well as the general direction (e.g., increase or decrease of the dosage rate). The dosage change indicator 2224 may be represented visually by one or more arrows, but could be represented by other shapes or objects, colors, or otherwise. Such an indicator could also be displayed for the vital sign information 2202, such as to show how the vital sign is changing over time.

The GUI 2200 may further include one or more indicator objects 2240A-2240D that can be presented on or near the chart/graph of historical data of the vital sign 2202 at specific points in time. It is contemplated that one or more features (e.g., orientation, size, color, shape, etc.) of each of the indicator objects 2240A-2240D can be varied to visually indicate different information.

For example, indicator object 2240A is represented by an upwardly pointing arrow and may indicate a status that is different from indicator object 2240B (represented by a downwardly pointing arrow), although the subject matter may overlap. While indicator object 2240C (represented by a square) may indicate different information than indicator objects 2240A-2240B, as the symbols are differently shaped. In a similar manner, indicator object 2240D may indicate a status and subject matter that is entirely different from indicator objects 2240A-2240C, as it has a different shape than indicator objects 2240A-2240C.

As discussed above, it is preferred that the specific position of the one or more indicator objects 2240A-2240D may be related to why the object was created. This could be, for example, a specific time when an anomaly or danger was detected, or information was received at that time which triggered an alarm/alert. Although four indicator objects are shown, it is contemplated that the number of indicator objects on the GUI 2200 will be based on the specific alerts or other information to be presented. Furthermore, it is contemplated that each of the indicator objects 2240A-2240D will remain associated to the specific time on the chart. Thus, as the chart updates to show a different time period, the indicator objects will move to the left until they are no longer shown or they are presented in a different manner, for example.

Preferably, each of the indicator objects 2240A-2240D may comprise a selectable object that can be clicked on or otherwise selected by a clinician or other medical professional.

As one example shown in FIG. 22B, upon selection of the first indicator object 2240A, a window 2250 can be overlayed on the GUI 2200 with the window 2250 containing a first set of information. Here, the first set of information concerns a stroke volume (S.V.) of the patient's heart and displays a value of the stroke volume at the point in time where the first indicator object 2240A is located on the graph.

As another example shown in FIG. 22C, upon selection of the fourth indicator object 2240D, a window 2252 can be overlayed on the GUI 2200 with the window 2252 containing a second set of information. Here, the second set of information concerns a cardiac output (C.O.) of the patient's heart and displays a value of the cardiac output at the point in time where the fourth indicator object 2240D is located on the graph.

Rather than cardiac output or stroke volume, it is contemplated that the information could alternatively include other pertinent information related to the patient's care. Such information may include, for example, a hear rate of the patient, a blood oxygen saturation level of the patient, a body temperature of the patient, a second vital sign of the patient, a change in dosage rate of the medication, a change in dosage rate of a second medication, and so forth.

It is especially preferred that the additional information contains or concerns information not otherwise reported on the GUI 2200. In this manner, the clinician or other medical professional can be alerted to pertinent information about the patient that may not be routinely presented on the GUI 2200 while monitoring the patient's vital sign and a dosage rate of the medication being administered.

With respect to the remaining numerals in each of FIGS. 22A-22C, the same considerations for like components with like numerals of FIG. 1A apply.

Figure 23:
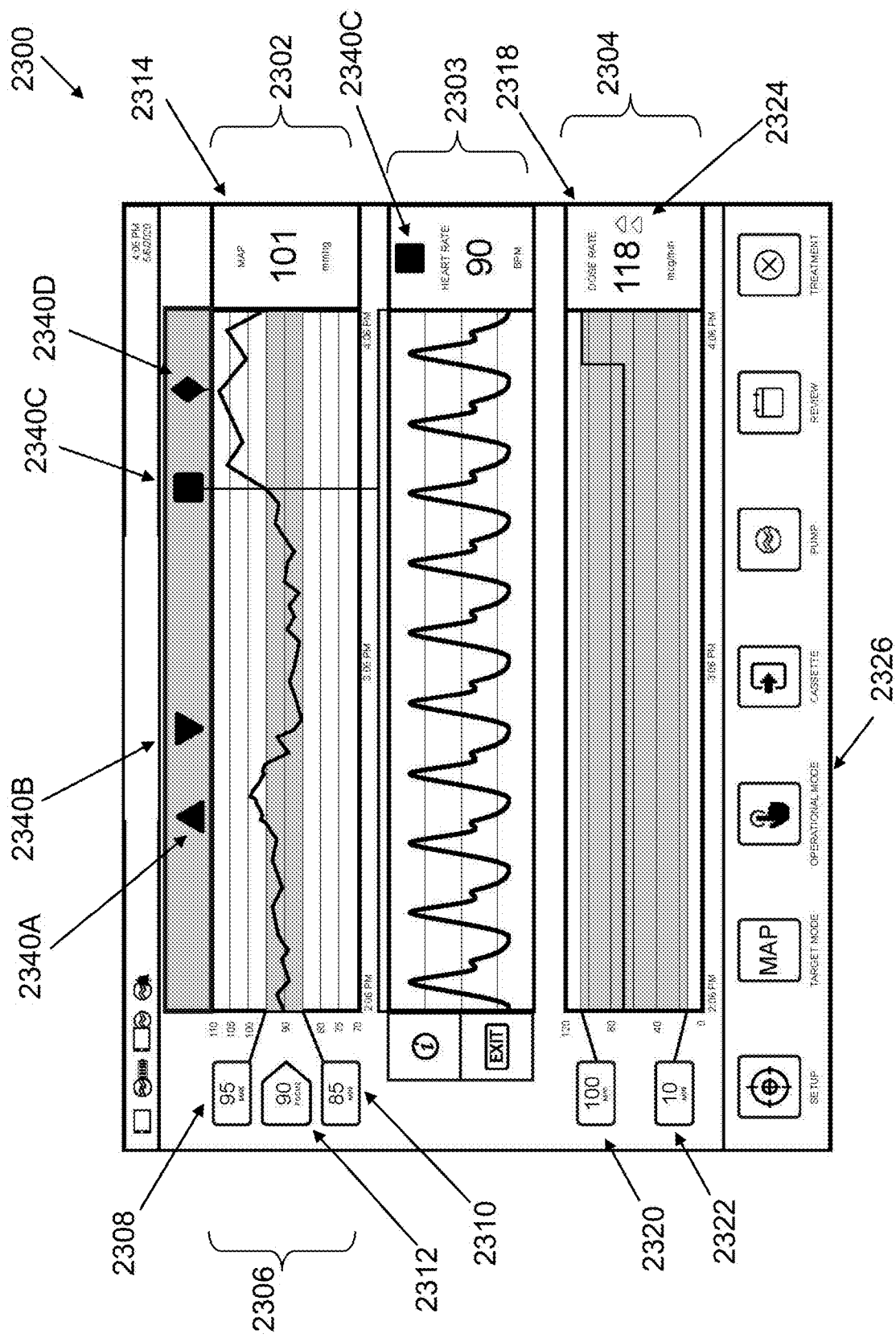
FIG. 23 illustrates another embodiment of an exemplary GUI presented on a display screen.
Figure 24:
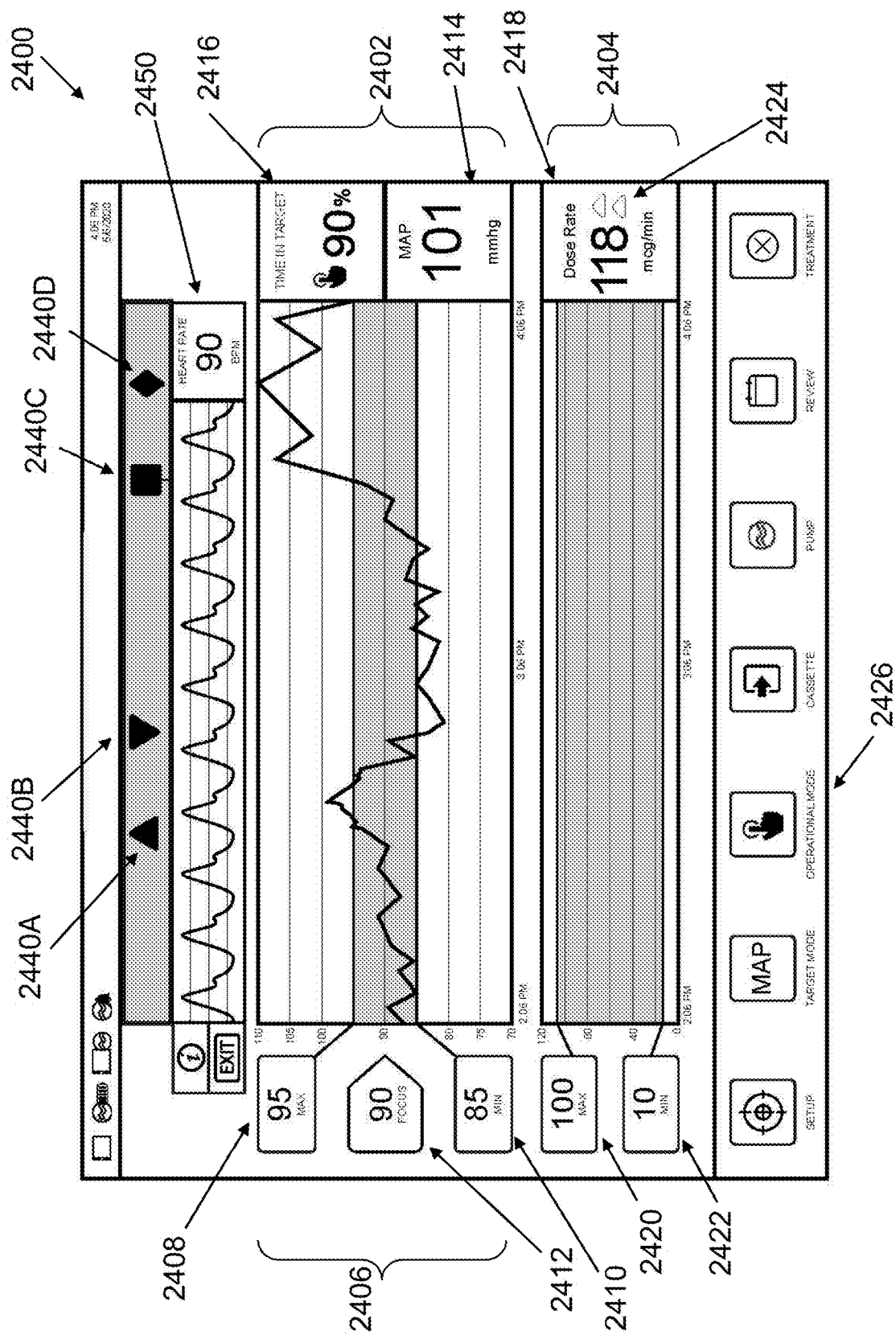
FIG. 24 illustrates another embodiment of an exemplary GUI presented on a display screen.

FIG. 23 illustrates another embodiment of a GUI 2300 for monitoring one or more vital signs of a patient that may be presented on a display screen of a device, for example. GUI 2300 is similar to the GUI described above and shown in FIG. 22A, except that selection of one of the indicator objects 2340A-2340D may display additional information related to the patient.

For example, upon selection of the third indicator object 2340C, information 2303 concerning the patient's heart rate may be presented on the GUI 2300 including a current value of a heart rate of the patient as well as historical data of the heart rate.

Upon selection of a different indicator object, it is contemplated that different information may be shown in place of the heart rate information 2303.

With respect to the remaining numerals in FIG. 23, the same considerations for like components with like numerals of FIG. 22A apply.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprise" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for monitoring a vital sign of a patient, comprising:
    presenting a graphic user interface (GUI) on a visual display screen;
    presenting a desired range of the vital sign of the patient on the GUI;
    presenting a current vital sign of a patient on the GUI received from a first source;
    presenting on the GUI a chart of historical data relating to the vital sign of the patient based upon information received from the first source;
    upon receiving a new vital sign of the patient, presenting the new vital sign and updating the historical data on the GUI;
    generating a first set of vital signs by selecting items of the historical data of a predefined time period;
    estimating a time in target value by determining an amount of elapsed time the first set of vital signs were within the desired range and dividing the amount of elapsed time by the predefined time period; and
    presenting the time in target value on the GUI.

2. The method of claim 1, wherein plotting the subset of the historical data on the GUI further comprises displaying the historical data in a graphical format depicting the vital sign of the patient over time.

3. The method of claim 2, wherein displaying the historical data in the graphical format further comprises displaying a time period object that is selectable to change the predefined time period.

4. The method of claim 1, further comprising:
    presenting a minimum dosage rate and a maximum dosage rate of a medication on the GUI;
    presenting a current dosage rate on the GUI;
    upon receiving a new dosage rate of the medication, saving the current dosage rate to historical rate data and presenting the new dosage rate on the GUI; and
    plotting a set of the historical rate data on the GUI.

5. The method of claim 4, further comprising:
    generating a dosage change indicator representing a change in the dosage rate between the current dosage rate and the new dosage rate; and
    presenting the dosage change indicator on the GUI.

6. The method of claim 4, further comprising:
    presenting an alert on the GUI if the current dosage rate falls outside of a range defined by the minimum dosage rate and the maximum dosage rate of the medication.

7. The method of claim 6, wherein the alert comprises a visual indicator on the GUI.

8. The method of claim 1, further comprising:
    presenting an alert on the GUI if the time in target value is less than a predetermined threshold.

9. The method of claim 1, further comprising:
presenting a first indicator object on the chart of the historical data at a specific time on the chart; and
upon selection of the first indicator object, presenting a first window overlayed on the GUI that comprises a first set of information.

10. The method of claim 9, wherein the information concerns an irregular heartbeat of the patient detected at the specific time.

11. The method of claim 9, wherein the information concerns a change in dosage rate of a medication in response to the current vital sign.

12. The method of claim 9, wherein the information concerns a second vital sign of the patient received from a second source.

13. The method of claim 1, further comprising:
displaying a manual management object that is selectable to switch from a closed-loop automated system for managing the vital sign and the current dosage rate to a manual system;
upon selection of the manual management object, generating a second set of vital signs by selecting items of the historical data falling within a second predefined time period, wherein the second predefined time period comprises at least a portion of a time when the manual system is activated by the manual management object;
estimating a second time in target value by determining an amount of time the second set of vital signs were within the desired range and dividing the amount of time by the second predefined time period; and
presenting on the GUI the time in target value and the second time in target value.

14. The method of claim 1, further comprising:
estimating a remaining amount of medication as a function of an initial volume of medication, the current dosage rate, and any historical dosage rate data; and
presenting the estimated remaining amount of medication on the GUI.

15. The method of claim 1, wherein the first vital sign comprises a mean arterial pressure of the patient, and wherein the first source comprises a transducer attached to the patient.

16. A system for managing a vital sign of a patient, comprising:
a display screen configured to present a graphical user interface (GUI);
a receiver adapted to receive information from a first source concerning a vital sign of a patient; and
a processor communicatively linked to the receiver to obtain the information from the first source and to the display screen to control the information presented on the GUI, wherein the processor is configured to present information concerning the vital sign and a medication being administered to the patient on the GUI;
wherein the GUI further comprises:
a current vital sign of the patient based on the information received from the first source;
a chart of historical data relating to the vital sign of the patient based on the information received from the first source;
a time in target value representing an amount of elapsed time the vital sign was within a predetermined range, wherein the processor is configured to (i) generate a first set of vital signs by selecting items of the historical data of a predefined time period, and (ii) estimate the time in target value by determining an amount of elapsed time the first set of vital signs were within the desired range and dividing the amount of elapsed time by the predefined time period.

17. The system of claim 16, wherein the GUI further comprises:
a minimum value and a maximum value that collectively define a desired range of the vital sign.

18. The system of claim 17, wherein the GUI further comprises:
a focus value for the vital sign.

19. The system of claim 18, wherein the focus value is not equal to a median value of a minimum value and a maximum value of a desired range for the vital sign.

20. The system of claim 16, wherein the GUI further comprises:
a minimum dosage rate of the medication;
a maximum dosage rate of the medication;
a current dosage rate of the medication being administered to the patient; and
second historical data relating to the dosage rate of the medication based on the information received from a second source.

21. The system of claim 20, wherein the GUI further comprises:
a dosage change indicator representing a change in the dosage rate between the current dosage rate and the new dosage rate.

22. The system of claim 16, wherein the GUI further comprises:
a time period object that is selectable to change the predefined time period.

23. The system of claim 16, wherein the processor is further configured to presenting an alert on the GUI upon receiving an alert command from an external source, and wherein the alert comprises a visual indicator on the GUI.

24. The system of claim 16, wherein the GUI further comprises:
a first indicator object on the chart of the historical data at a specific time on the chart; and
upon selection of the first indicator object, the processor causes a first window to be overlayed on the GUI, wherein the first window comprises a first set of information.

25. The system of claim 24, wherein the information concerns an irregular heartbeat of the patient detected by the processor at the specific time.

26. The system of claim 24, wherein the information concerns a change in dosage rate of a medication in response to the current vital sign.

27. The system of claim 24, wherein the information concerns a second vital sign of the patient received by the receiver from a second source.

28. The system of claim 16, wherein the GUI further comprises a manual management object that is selectable to switch the system from a closed-loop automated system for managing the vital sign and the current dosage rate to a manual system, and the system further comprising:
upon selection of the manual management object, the processor is configured to generate a second set of vital signs by selecting items of the historical data falling within a second predefined time period, wherein the second predefined time period comprises at least a portion of a time when the manual system is activated by the manual management object;
estimating a second time in target value by determining an amount of time the second set of vital signs were within the desired range and dividing the amount of time by the second predefined time period; and presenting on the GUI the time in target value and the second time in target value.

29. The system of claim 16, wherein the processor is further configured to estimate a remaining amount of medication as a function of an initial volume of medication, the current dosage rate, and any historical dosage rate data, and wherein the GUI further comprises the estimated remaining amount of medication.

30. The system of claim 16, wherein the first vital sign comprises a mean arterial pressure of the patient, and wherein the first source comprises a transducer attached to the patient.

* * * * *